US008131471B2

(12) United States Patent
Kincaid

(10) Patent No.: US 8,131,471 B2
(45) Date of Patent: *Mar. 6, 2012

(54) METHODS AND SYSTEM FOR SIMULTANEOUS VISUALIZATION AND MANIPULATION OF MULTIPLE DATA TYPES

(75) Inventor: Robert Kincaid, Half Moon Bay, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 1693 days.

This patent is subject to a terminal disclaimer.

(21) Appl. No.: 10/688,588

(22) Filed: Oct. 18, 2003

(65) Prior Publication Data

US 2004/0061702 A1  Apr. 1, 2004

Related U.S. Application Data

(63) Continuation-in-part of application No. 10/403,762, filed on Mar. 31, 2003.

(60) Provisional application No. 60/402,566, filed on Aug. 8, 2002.

(51) Int. Cl.
*G01N 33/48* (2006.01)
*G01N 33/50* (2006.01)

(52) U.S. Cl. .................................................. 702/19

(58) Field of Classification Search ........................ None
See application file for complete search history.

(56) References Cited

U.S. PATENT DOCUMENTS

| | | | |
|---|---|---|---|
| 5,632,009 A | 5/1997 | Rao et al. | |
| 5,826,260 A * | 10/1998 | Byrd et al. | 707/5 |
| 5,864,838 A * | 1/1999 | Rusterholz | 1/1 |
| 5,880,742 A | 3/1999 | Rao et al. | |
| 6,085,202 A | 7/2000 | Rao et al. | |
| 6,185,561 B1 * | 2/2001 | Balaban et al. | 707/6 |
| 6,424,973 B1 | 7/2002 | Baclawski | |
| 6,884,578 B2 * | 4/2005 | Warrington et al. | 435/6 |
| 7,035,739 B2 | 4/2006 | Schadt | |
| 7,038,680 B2 * | 5/2006 | Pitkow | 345/440 |
| 7,118,853 B2 | 10/2006 | Botstein | |
| 7,243,112 B2 | 7/2007 | Qu | |
| 7,472,137 B2 | 12/2008 | Edelstein et al. | |
| 2002/0021299 A1 * | 2/2002 | Tamura et al. | 345/440 |
| 2002/0174096 A1 | 11/2002 | O'Reilly et al. | |
| 2002/0194176 A1 * | 12/2002 | Gruenwald | 707/7 |
| 2003/0028501 A1 * | 2/2003 | Balaban et al. | 707/1 |
| 2003/0124539 A1 * | 7/2003 | Warrington et al. | 435/6 |
| 2004/0019466 A1 * | 1/2004 | Minor et al. | 702/190 |
| 2005/0034107 A1 | 2/2005 | Kendall et al. | |

FOREIGN PATENT DOCUMENTS

| | | |
|---|---|---|
| EP | 1 388 801 A2 | 2/2004 |
| WO | WO 01/27809 A2 | 4/2001 |

OTHER PUBLICATIONS

"Agilent Synapsia Informatics Workbench", Agilent Technologies, Inc., Printed in the USA, Jul. 31, 2002.

"A Tribute to J. Bertin's Graphical Data Analysis", Antoine de Falguerolles Laboratoire de Statistique et Probabilie's, UMR CNRS Universite' Paul Sabatier 118 route de Narbonne, Nov. 29, 1996.
Kandogan, E., "Star Coordinates: A Multi-dimensional Visualization Technique with Uniform Treatment of Dimensions", IBM Almaden Research Center, not dated.
Felsenstein, J. "SEQBOOT—Bootstrap, Jackknife, or Permutation Resampling of Molecular Sequence, Restriction Site, Gene Frequency or Character Data", copyright 1991-1993 by the University of Washington and Josepn Felsenstein.
Bittner et al., "Molecular classification of cutaneous malignant melanoma by gene expression profiling", Nature, vol. 406,pp. 536-540, Aug. 2000.
Luo et al., "Human Prostate Cancer and Benign Prostatic Hyperplasia: Molecular Dissection by Gene Expression Profiling", Cancer Research 61, 4683-4688, Jun. 15, 2001.
Kincaid, "Interactive Poster: VistaClara: An Interactive Visualization for Microarray Data Exploration", submitted Jul. 2003 for InfoVis 2003 Conference http://infovis.org/infovis2003/.
Kincaid, "VistaClara: An Interactive Visualization for Exploratory Analysis of DNA Microarray", submission for publication on Aug. 29, 2003, to SAC 2004, http://www.cs.iupui.edu/ bioin/.
Slonim, "From patterns to pathways: gene expression data analysis comes of age", Nature Genetics Supplement, vol. 32, pp. 502-508, Dec. 2002.
Clare et al., How well do we understand the clusters found in microarray data? 2002, pp. 1-12.
Eisen et al., Cluster analysis and display of genome-wide expression patterns. vol. 95, 1998, pp. 14863-14868.
Friedman et al., GENIES: A natural-language processing system for the extraction of molecular pathways from journal articles. vol. 17, 2001, pp. S74-S82.
Fellenberg et al., Microarray data warehouse allowing for inclusion of experiment annotations in statistical analysis. vol. 18, No. 3, 2002, pp. 423-433.
Krauthammer et al., Of truth and pathways: chasing bits of information through myriads of articles. vol. 18, 2002, pp. S249-S257.
Weinstein et al., An Information-Intensive Approach to the Molecular Pharmacology of Cancer. vol. 275, 1997, pp. 343-349.
Raychaudhuri, Soumya, Chang, Jeffrey, Sutphin, Patrick and Altman, Russ, Associating Genes with Gent Ontology Codes Using a Maximum Entropy Analysis of Biomedical Literature, Cold Spring Harbor Laboratory Press, Genome Research, vol. 12, pp. 203-214, Jan. 2002.
Karp, Peter. An Ontology for Biological Function Based on Molecular Interactions. Oxford University Press. 2000. vol. 16. No. 3, pp. 269-285.
U.S. Appl. No. 11/128,896 Non Final Office Action dated Mar. 23, 2009.
U.S. Appl. No. 10/403,762 Non Final Office Action dated Dec. 16, 2008.
Pollack, et al, Genome Wide Analysis of DNA Copy-Number Changes Using cDNA Microarrays, Nature Genetics, vol. 23. 1999 pp. 41-46.
U.S. Appl. No. 10/817,244 Non Final Office Action dated Nov. 14, 2008.

* cited by examiner

*Primary Examiner* — Jason Sims

(57) ABSTRACT

Software systems, methods and recordable media for organizing and manipulating diverse data sets to facilitate identification, trends, correlations and other useful relationships among the data. Extremely large data sets such as microarray data and other biological data are graphically displayed and sorted in an effort to develop visual similarities, correlations or trends that can be seen by a user of the present invention. Various schemes for graphical representations of the data, as well as sorting schemes are provided, including sorting schemes performed relative to pseudo-data vectors.

16 Claims, 12 Drawing Sheets

| | UACC-1012 | UACC-1529 | UACC-647 | WM1791-C | UACC-827 | HA-A | UACC-930 | UACC-903 | UACC-1097 | M93-47 | TD-1720 | TD-1638 | TD-1730 | |
|---|---|---|---|---|---|---|---|---|---|---|---|---|---|---|
| | | | | | | | | | | | | | | solute carrier family 16 (mono carboxylic acid tr |
| | | | | | | | | | | | | | | homeo box D3 |
| | | | | | | | | | | | | | | cerebellin 1 precursor |
| | | | | | | | | | | | | | | chemokine (C-X-C motif), receptor 4 (fusin) |
| | | | | | | | | | | | | | | multispanning membrane protein (70kD) |
| | | | | | | | | | | | | | | ataxia telangiectasia and Rad3 related |
| | | | | | | | | | | | | | | profilin 1 |
| | | | | | | | | | | | | | | forkhead (Drosophilia)-like 1 |
| | | | | | | | | | | | | | | ESTs, Highly similar to CGI-03 protein (H sapie |
| | | | | | | | | | | | | | | Homo sapiens mRNA: cDNA DKFZp564B0769 |
| | | | | | | | | | | | | | | ESTs |
| | | | | | | | | | | | | | | ESTs |
| | | | | | | | | | | | | | | ESTs |
| | | | | | | | | | | | | | | RAB5A, member RAS oncogene family |
| | | | | | | | | | | | | | | uno-51 (C elegans)-like kinase 1 |
| | | | | | | | | | | | | | | protein tyrosine phosphatase, receptor type, ga |
| | | | | | | | | | | | | | | disabled (Drosophilia) homolog 2 (mitogen-resp |
| | | | | | | | | | | | | | | ESTs |
| | | | | | | | | | | | | | | RAB111A, member RAS oncogene family |
| | | | | | | | | | | | | | | antiquitin 1 |
| | | | | | | | | | | | | | | major histocompatibility complex, class II, Dp b |
| | | | | | | | | | | | | | | fucosyltransferase 8 (alpha (1,6) fucosyltransfe |
| | | | | | | | | | | | | | | tumor protein D52 |
| | | | | | | | | | | | | | | cleavage stimulation factor, 3' pre-RNA, subuni |

| | UniGene | Clone | Name | BNS_Sym | BNS_Desc | BNS_Chr | TC... | U... | UA... | | U... | HA... | U... | U... | | U... | M9... | M9... |
|---|---|---|---|---|---|---|---|---|---|---|---|---|---|---|---|---|---|---|
| 1 | Invasive Ability | | | | | | | | 4.9 | | 3.9 | 4.8 | 3.8 | | | | 2.6 |
| 2 | Vasulogenic Mimricy | | | | | | | | | | +/- | +/- | + | | | | - |
| 3 | Cell Motility | | | | | | | | | | | | | | | | |
| 4 | Sex | | | | | | | M | M | | F | F | F | M | | | M | F |
| 5 | Hs.23590 | 141562.0 | solute carrier f | SLC16A4 | solute carrier f | 1p12 | | | | | | | | | | | | |
| 6 | Hs.93574 | 724112.0 | homeo box D3 | HOXD3 | homeo box D3 | 2q31-q37 | | | 122.0 | | | | | | | | | |
| 7 | Hs.662 | 768357.0 | cerebellin 1 pr | CB | | | | | | | | | | | | | | |
| 8 | Hs.89444 | 79629.0 | chemokine (C- | CX | | | | | | | | | | | | | | |
| 9 | Hs.91585 | 490306.0 | multispanning | TM | | | | | | | | | | | | | | |
| 10 | Hs.77613 | 842906.0 | ataxia telangie | AT | | | | | | | | | | | | | | |
| 11 | Hs.75721 | 826173.0 | profilin 1 | PFN1 | profilin 1 | 17p13.3 | | | | | | | | | | | | |
| 12 | Hs.2714 | 33051.0 | forkhead (Dros | FOXG1B | forkhead BOX | 14q12-q13 | | | | | | | | | | | | |
| 13 | Hs.247469 | 344282.0 | ESTs, Highly s | | | | | | | | | | | | | | | |
| 27 | Hs.2384 | 120544.0 | tumor protein | TPD52 | tumor protein | 8q21 | | | | | | | | | | | | |
| 29 | Hs.183656 | 297439.0 | Ests | VNN3 | vanin 3 | 6q23-q24 | | | | | | | | | | | | |
| 31 | Hs.14355 | 297439.0 | Ests | | | | | | | | | | | | | | | |
| 32 | Hs.15740 | 134829.0 | Homo sapiens | | | | | | | | | | | | | | | |
| 33 | Hs.182817 | 1418.0 | Ests | | | | | | | | | | | | | | | |
| 34 | Hs.241065 | 296 | | | | | | | | | | | | | | | | |
| 35 | Hs.82572 | 281 | | | | | | | | | | | | | | | | |
| 36 | Hs.76465 | 358 | | | | | | | | | | | | | | | | |
| 37 | Hs.22466 | 809 | | | | | | | | | | | | | | | | |
| 38 | Hs.155101 | 502 | | | | | | | | | | | | | | | | |
| 59 | Hs.84746 | 724615.0 | chromosome c | CHC1 | chromosome c | 1p36.1 | | | | | | | | | | | | |

Clinical Data

1 Gene Many Microarrays

1 Microarray Many genes

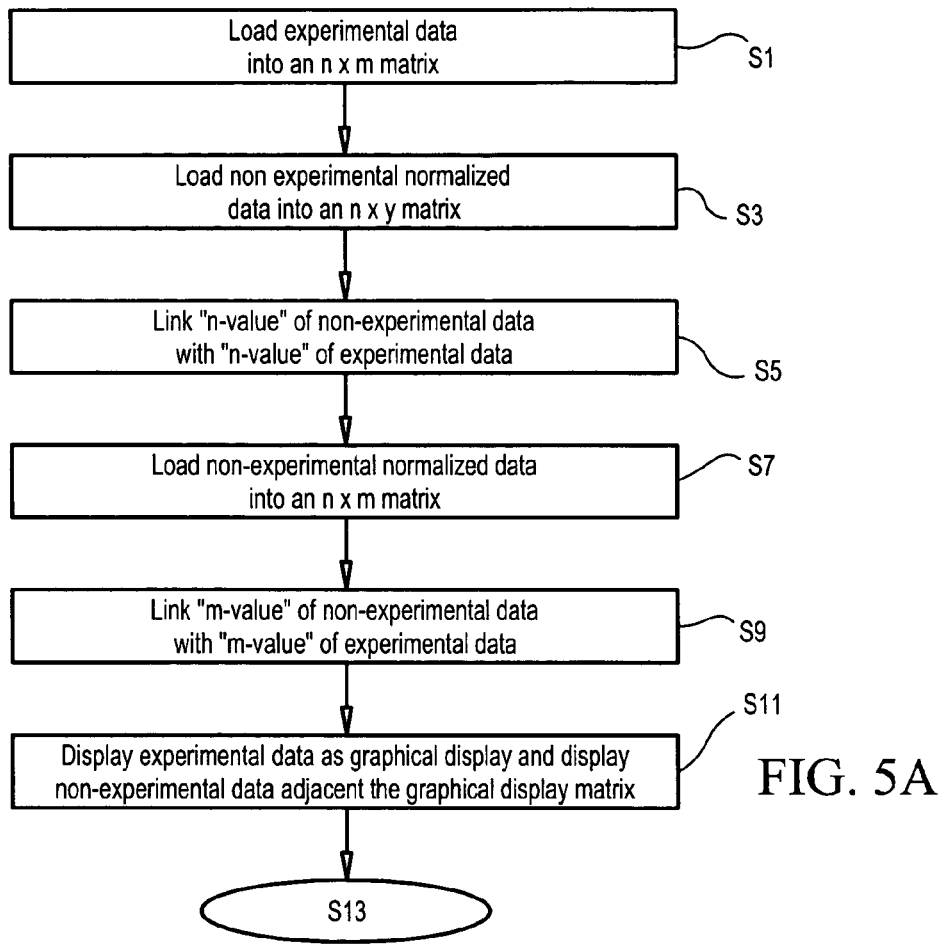
FIG. 5A
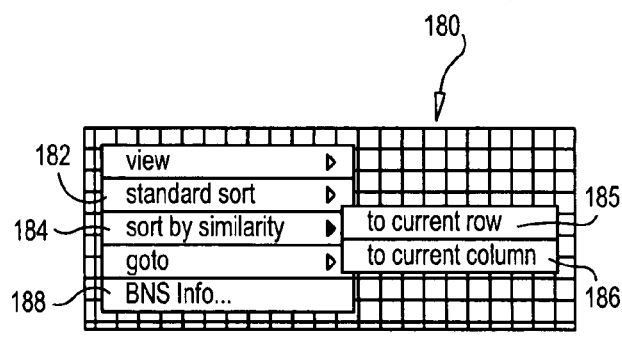
FIG. 6A
FIG. 6B

| | 101 | 102 | 103 |
|---|---|---|---|
| 202 | 101,202 | 102,202 | 103,202 |
| 201 | 101,201 | 102,201 | 103,201 |
| 203 | 101,203 | 102,203 | 103,203 |
| 204 | 101,203 | 102,203 | 103,203 |
FIG. 6C
| | 101 | 102 | 103 |
|---|---|---|---|
| 202 | 101,202 | 102,202 | 103,202 |
| 203 | 101,203 | 102,203 | 103,203 |
| 201 | 101,201 | 102,201 | 103,201 |
| 204 | 101,204 | 102,204 | 103,204 |
FIG. 6D
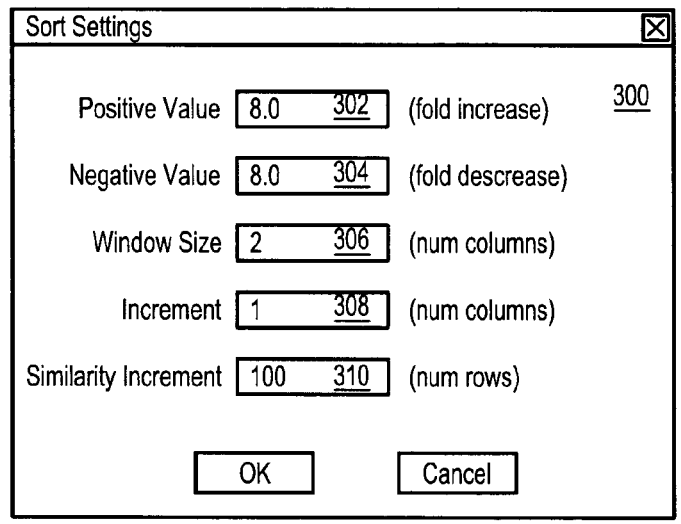
FIG. 9A
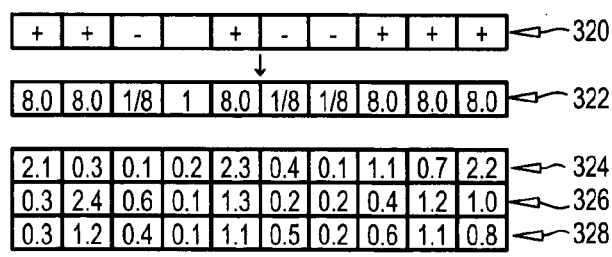
FIG. 9B

FIG. 7

FIG. 10

METHODS AND SYSTEM FOR SIMULTANEOUS VISUALIZATION AND MANIPULATION OF MULTIPLE DATA TYPES

CROSS-REFERENCE

This application is a continuation-in-part application of application Ser. No. 10/403,762, filed Mar. 31, 2003, which claims the benefit of Provisional Application No. 60/402,566, filed Aug. 8, 2002. Application Ser. No. 10/403,762 and Provisional Application No. 60/402,566 are both incorporated herein, in their entireties, by reference thereto, and to which applications we claim priority under 35 USC §120.

FIELD OF THE INVENTION

The present invention pertains to software systems and methods for organizing and manipulating diverse data sets to facilitate identification, trends, correlations and other useful relationships among the data.

BACKGROUND OF THE INVENTION

The advent of new experimental technologies that support molecular biology research have resulted in an explosion of data and a rapidly increasing diversity of biological measurement data types. Examples of such biological measurement types include gene expression from DNA microarray or Taqman experiments, protein identification from mass spectrometry or gel electrophoresis, cell localization information from flow cytometry, phenotype information from clinical data or knockout experiments, genotype information from association studies and DNA microarray experiments, etc. This data is rapidly changing. New technologies frequently generate new types of data.

Understanding observed trends in gene or protein expression often require correlating this data with additional information such as phenotype information, clinical patient data, putative drug treatments dosages, graphical representation of biological information, etc. Even when fairly rigorous computational techniques such as machine learning-based clustering or classification schemes are used, the results of these techniques are typically cross-checked with observed phenotypes or clinical diagnoses to interpret what the computational results might mean.

Currently, correlations of the experimental data with types of additional information as exemplified above are often done by manually (i.e., visually) inspecting the additional (e.g., clinical) data and visually comparing it with the experimental data to look for similarities (i.e., correlations) between experimental and observed phenomena. For example, a researcher might notice a highly up or down regulated gene during inspection of a microarray experiment and then explore the available clinical data to see if any observed clinical data correlates with the known function of the gene involved in the microarray experiment. Finding correlations in this manner could be described as a "hit-or-miss" procedure and is also dependent upon the accumulated knowledge of the researcher. Further, the large volumes of data that are generated by current experimental data generating procedures, such as microarray procedures, for example, make this method of correlating an extremely tedious, if not impossible task.

Efforts at consolidating the data to be analyzed for correlations between experimental results and observed phenomena have been made by attempting to consolidate all the data to be viewed into massive spreadsheets or tabular displays. However, the usefulness of these types of approaches has been limited because, due to the sheer volumes of data that usually need to be analyzed, it becomes impossible to view all relevant experimental data together, at once, on a single screen to allow visual comparison. Accordingly, it becomes necessary to provide split views, scrolling or multiple windows in order to view all of the data needed for performing the analysis. Not only does this make it difficult to easily make visual comparisons among the data contained in different screens, windows or views, but the ability to manipulate the data so as to make visual comparisons according to different characterizations of the data (different types of sorting, clustering, classification, etc.) to search for trends, correlations or other insights, becomes unwieldy and problematic.

Efforts have been made in attempting to visualize and discover overall gene expression patterns from large gene expression data sets with little success. For example, scatter plots and parallel coordinate techniques available with Spotfire 4.0 and Spotfire 5.0 were used by Pan in an attempt to identify expressed sequence tags (ESTs) having expression patterns similar to those of known genes. Both the expression patterns of the ESTs as well as those of the known genes were obtained from a data set including melanoma samples and normal (control) samples provided by National Human Genome Research Institute (see Pan, Zhijian: "Application Project: Visualized Pattern Matching of Malignant Melanoma with Spotfire and Table Lens", http//:www.cs.umd.edu/class/spring2001/cmsc838b/Apps/presentations/Zhijian_Pan/. The use of scatter plots was reported to be incapable of managing the complexity of the data set being examined. The use of parallel coordinates with Spotfire 5.0 was more promising, in that it was capable of displaying all thirty-eight experimental conditions on a single page, where similarities in expression patterns could be searched for.

Table Lens was also employed by the same researcher to visualize expression patterns of the ESTs and known genes. However, it was reported that Table Lens was ineffective, and "very difficult" for use in finding matching patterns. Neither Spotfire (4.0 or 5.0) was used to compare expression or other experimental data with supporting clinical data or data sets of any other type, but were only used in attempting to group like data within the experimental data set.

A tool for forming a compressed view of gene expression results from multiple microarrays is described in co-pending and commonly owned application Ser. No. 10/209,477 filed Jul. 30, 2002 and titled "Method of Identifying Trends, Correlations, and Similarities Among Diverse Biological Data Sets and System for Facilitating Identification", which is incorporated herein in its entirety, by reference thereto. In one example, microarray experimental data used to generate the compressed visualization was obtained from the National Human Genome Research Institute of the National Institutes of Health. Experiments were performed with respect to thirty-one subcutaneous melanoma patients using DNA microarrays. For each patient, eight thousand and sixty-six individual microarray measurements were displayed. Additionally, clinical data as well as patient cluster, and gene specific annotations corresponding to the gene represented by the expression ratios were contained within the respective rows of microarray data. Since the data set is highly de-normalized, for a given patient, the data in the clinical columns was repeated for each gene measured by that patient's microarray. In order to display such a massive number of columns in a single visualization, this system also employed Table Lens, which allowed the diverse data sets to be compressed, displayed and inspected simultaneously in graphical form on a single display. In this example, the system was based on a product known as Eureka, by Inxight. A complete description of the functionality of Table Lens can be found in U.S. Pat. Nos. 5,632,009; 5,880,742 and 6,085,202, each of which is incorporated herein, in its entirety, by reference thereto. The resultant visualization was a very dense graphical display representing 241,980 rows of data entirely visible on a single standard computer display. The visualization was highly compressed, with graphical values displayed to represent groups of cell values, since the compression prevented each individual row or cell value from being displayed. The tool further provides the capability of sorting by various data categories, such as "patient cluster" and "invasive ability", for example, as described in the application. As a result of such sorting operations, correlation may be observed between patient clusters, or other categorical criteria. Although the system and methods described in the above system can be very useful and powerful in preparing visualizations for the analysis of biological analysis, they also require a significant amount of learning and familiarization with what is otherwise a quite non-intuitive display for those trained in the biological research disciplines. Those users that have not dedicated enough time to fully understand how to manipulate and interpret the display are likely to be confused or intimidated by the graphical representations of the compressed data and as to how to interpret them.

More powerful methods of combining widely diverse, but related and potentially correlated biological data sets are needed to improve the ease, speed and efficiency of correlating information in these data sets. Further, more powerful methods are needed to improve the probability that such correlations will be identified.

SUMMARY OF THE INVENTION

The present invention provides systems, methods and recordable media for manipulating large data sets for visually identifying relationships among the data that can be useful to a researcher. By manipulating the data according to the present methods, sorting of the data may be accomplished relative to one or more pseudo-data vectors calculated from any of a variety of sources. Data can be easily and quickly manipulated by sorting or reordering rows or columns to expose potentially meaningful correlations and trends in the data which are easily observed.

A pseudo-data vector may be calculated from data that is descriptive of the dataset being examined, but not part of the actual data in the dataset. A pseudo-data vector may be calculated from an entire row (or column) of descriptive data, or even only a portion thereof, for example when one or more data values are missing from the row or column of descriptive data. User input may be provided for, wherein a user or the system may input predetermined values to be substituted for the descriptive data values.

A pseudo-vector may be calculated from arbitrary data input from a user.

A pseudo-data vector may be calculated by selecting a portion of a row (or column) of the data in the dataset, wherein the selected portion is emphasized by assigning a preset positive value to each cell value in the selected portion, and wherein a null or negative preset negative value is assigned to all cell values which have not been selected in the row or column.

A multi-step method of sorting is also disclosed wherein only portions of the data are reordered at each step, each time based upon a different pseudo-data vector.

The present invention also covers forwarding, transmitting, and/or receiving a result obtained from any of the methods or methods steps covered.

A variety of different techniques for graphically representing the data are also disclosed, as well as various sorting and sub-sorting techniques. Additionally, docking features are provided for combining predefined matrices of similar or disparate data.

The present invention provides extremely powerful techniques for visualizing the massive datasets generated by high-throughput experiments such as DNA microarrays. Further, the results of these experiments can be visually manipulated to look for trends and correlations using simple human intelligence in lieu of more sophisticated analytical tools such as clustering or classification algorithms. Nothing precludes using these algorithmic tools, and the calculated data can even be incorporated into the dataset being examined by the invention. However, the human mind has adapted over evolution to have powerful pattern matching abilities, and this visualization leverages this ability to permit a high degree of ad-hoc high-level analysis and discovery to be performed. Algorithmic techniques are quite powerful, but usually directed toward looking at specific pre-defined correlations or trends. This invention allows approaching the data with no particular predisposition and can be used to provide insight as to which computational techniques might be useful.

These and other advantages and features of the invention will become apparent to those persons skilled in the art upon reading the details of the systems and methods as more fully described below.

BRIEF DESCRIPTION OF THE DRAWINGS

FIG. 1 shows an example of a portion of a conventional heat map visualization 200 that is currently available to users.

FIG. 2 shows a screen display 100 resultant from using a visualization system according to the present invention.

FIG. 3 shows a screen display resulting from performing a column sort on the data shown in FIG. 2.

FIG. 4 shows the display order resulting after a row sort was performed subsequent to column sort described with regard to FIG. 3.

FIGS. 5A-5B show a flow chart which outlines basic procedures for preparing and displaying a visualization using the system according to the present invention, and for the manipulations of the data displayed.

FIG. 6A shows a simple 3×4 matrix referred to for purposes of demonstrating concepts of similarity sorting according to the present invention.

FIG. 6B shows a popup menu that may be invoked by the user to perform sorting manipulations and/or access additional annotation data.

FIG. 6C shows the matrix of FIG. 6A, after selection of row 202 for performance of a similarity sort based thereon according to the present invention.

FIG. 6D shows the resulting order of the cells of the matrix after performing a similarity sort based upon the selection shown in FIG. 6C.

FIG. 7 shows the results of a similarity row sort according to the present invention, wherein the sort was based upon the row identified as gene "DUSP1".

FIG. 9A shows an example of a menu item available to a user for setting pseudo-values to be assigned to binary data according to the user's preferences.

FIG. 9B schematically shows a classification row 320 having binary values, being converted to a pseudo-experimental vector to be used as a basis for similarity sorting.

FIG. 10 shows the results of a similarity sort carried out against a pseudo-data vector in accordance with techniques and tools provided by the present invention.

DETAILED DESCRIPTION OF THE INVENTION

Figure 5B:
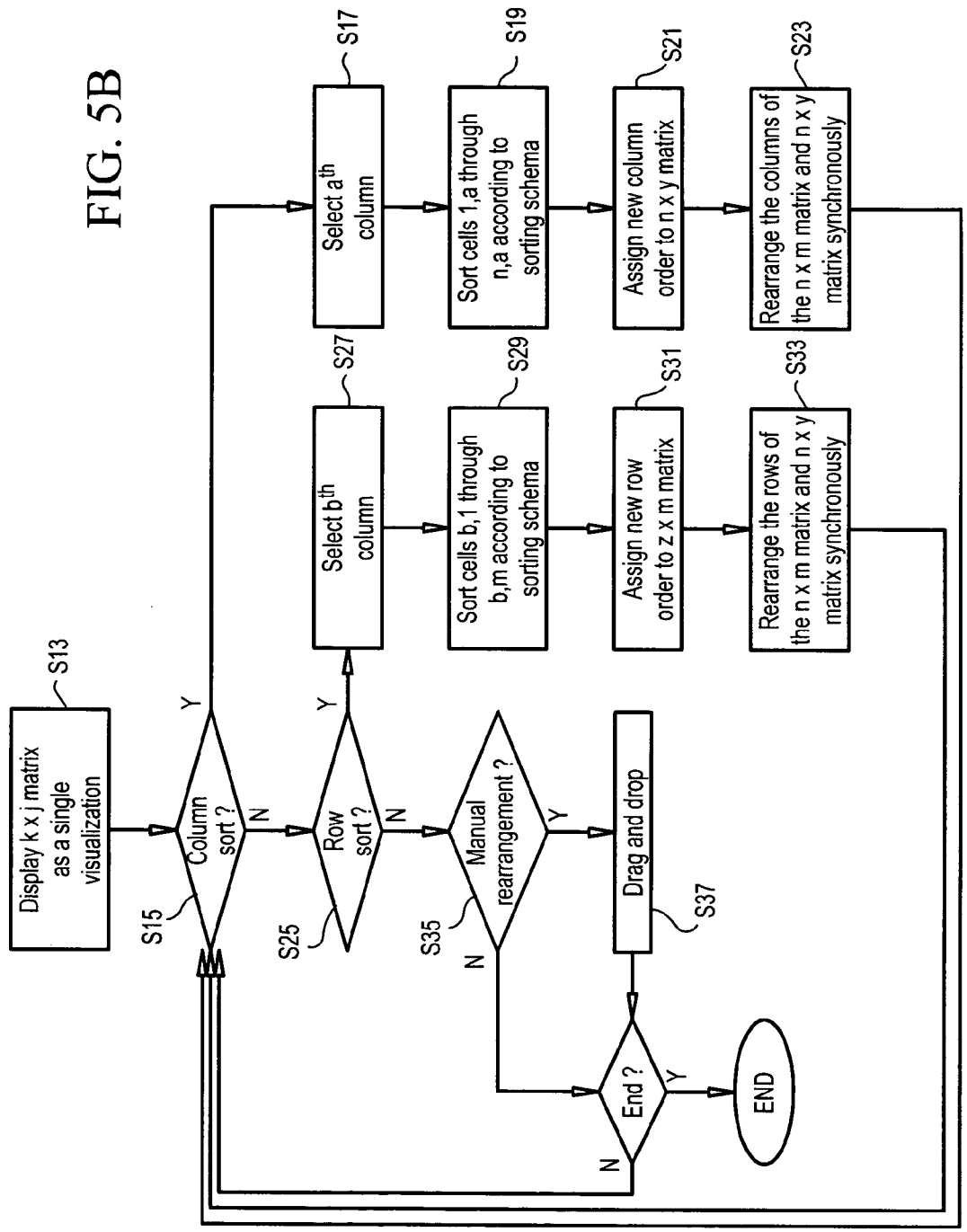

Before the present methods, tools and system are described, it is to be understood that this invention is not limited to particular data sets, manipulations, tools or steps described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a gene" includes a plurality of such genes and reference to "the array" includes reference to one or more arrays and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

The term "cell", when used in the context describing a data table or heat map, refers to the data value at the intersection of a row and column in a spreadsheet-like data structure or heat map; typically a property/value pair for an entity in the spreadsheet, e.g. the expression level for a gene.

"Color coding" refers to a software technique which maps a numerical or categorical value to a color value, for example representing high levels of gene expression as a reddish color and low levels of gene expression as greenish colors, with varying shade/intensities of these colors representing varying degrees of expression. Color-coding is not limited in application to expression levels, but can be used to differentiate any data that can be quantified, so as to distinguish relatively high quantity values from relatively low quantity values. Additionally, a third color can be employed for relatively neutral or median values, and shading can be employed to provide a more continuous spectrum of the color indicators.

The term "data mining" refers to a computational process of extracting higher-level knowledge from patterns of data in a database. Data mining is also sometimes referred to as "knowledge discovery".

The term "down-regulation" is used in the context of gene expression, and refers to a decrease in the amount of messenger RNA (mRNA) formed by expression of a gene, with respect to a control.

"Gel electrophoresis" refers to a biological technique for separating and measuring amounts of protein fragments in a sample. Migration of a protein fragment across a gel is proportional to its mass and charge. Different fragments of proteins, prepared with stains, will accumulate on different segments of the gel. Relative abundance of the protein fragment is proportional to the intensity of the stain at its location on the gel.

The term "gene" refers to a unit of hereditary information, which is a portion of DNA containing information required to determine a protein's amino acid sequence.

"Gene expression" refers to the level to which a gene is transcribed to form messenger RNA molecules, prior to protein synthesis.

"Expression data" or "gene expression data" refers to quantitative representations of gene expressions.

"Gene expression ratio" is a relative measurement of gene expression, wherein the expression level of a test sample is compared to the expression level of a reference sample.

A "gene product" is a biological entity that can be formed from a gene, e.g. a messenger RNA or a protein.

A "heat map" or "heat map visualization" is a visual representation of a tabular data structure of gene expression values, wherein color-codings are used for displaying numerical values. The numerical value for each cell in the data table is encoded into a color for the cell. Color encodings run on a continuum from one color through another, e.g. green to red or yellow to blue for gene expression values. The resultant color matrix of all rows and columns in the data set forms the color map, often referred to as a "heat map" by way of analogy to modeling of thermodynamic data.

A "hypothesis" refers to a provisional theory or assumption set forth to explain some class of phenomenon.

An "item" refers to a data structure that represents a biological entity or other entity. An item is the basic "atomic" unit of information in the software system.

The term "mass spectrometry" refers to a set of techniques for measuring the mass and charge of materials such as protein fragments, for example, such as by gathering data on trajectories of the materials/fragments through a measurement chamber. Mass spectrometry is particularly useful for measuring the composition (and/or relative abundance) of proteins and peptides in a sample.

A "microarray" or "DNA microarray" is a high-throughput hybridization technology that allows biologists to probe the activities of thousands of genes under diverse experimental conditions. Microarrays function by selective binding (hybridization) of probe DNA sequences on a microarray chip to fluorescently-tagged messenger RNA fragments from a biological sample. The amount of fluorescence detected at a probe position can be an indicator of the relative expression of the gene bound by that probe.

The term "normalize" refers to a technique employed in designing database schemas. When designing efficiently stored relational data, the designer attempts to reduce redundant entries by "normalizing" the data, which may include creating tables containing single instances of data whenever possible. Fields within these tables point to entries in other tables to establish one to one, one to many or many to many relationships between the data. In contrast, the term "de-normalize" refers to the opposite of normalization as used in designing database schemas. De-normalizing means to flatten out the space efficient relational structure resultant from normalization, often for the purposes of high speed access that avoid having to follow the relationship links between tables.

The term "promote" refers to an increase of the effects of a biological agent or a biological process.

A "protein" is a large polymer having one or more sequences of amino acid subunits joined by peptide bonds.

The term "protein abundance" refers to a measure of the amount of protein in a sample; often done as a relative abundance measure vs. a reference sample.

"Protein/DNA interaction" refers to a biological process wherein a protein regulates the expression of a gene, commonly by binding to promoter or inhibitor regions.

"Protein/Protein interaction" refers to a biological process whereby two or more proteins bind together and form complexes.

The term "pseudo-data vector" refers to a vector containing pseudo values based on inputs by a user of the system, which is constructed for performing similarity sorts against actual data vectors generated from a dataset.

The term "pseudo-data" refers to data values generated for the construction of a pseudo-data vector for performing similarity sorts with respect to actual data. Pseudo-data is based on user input, and may be further dependent upon binary data relating to the actual data, or upon a selection from the actual data.

The terms "pseudo-experimental vector" and "pseudo-experimental data vector" refer to a pseudo-data vector arranged to perform similarity sorts with respect to experimental data.

The terms "pseudo-expression vector" and "pseudo-expression data vector" refer to a pseudo-data vector arranged to perform similarity sorts with respect to expression data.

A "sequence" refers to an ordered set of amino acids forming the backbone of a protein or of the nucleic acids forming the backbone of a gene.

The term "overlay" or "data overlay" refers to a user interface technique for superimposing data from one view upon data in a different view; for example, overlaying gene expression ratios on top of a compressed matrix view.

A "spreadsheet" is an outsize ledger sheet simulated electronically by a computer software application; used frequently to represent tabular data structures.

The term "up-regulation", when used to describe gene expression, refers to an increase in the amount of messenger RNA (mRNA) formed by expression of a gene, with respect to a control.

The term "UniGene" refers to an experimental database system which automatically partitions DNA sequences into a non-redundant sets of gene-oriented clusters. Each UniGene cluster contains sequences that represent a unique gene, as well as related information such as the tissue types in which the gene has been expressed and chromosome location.

The term "view" refers to a graphical presentation of a single visual perspective on a data set.

The term "visualization" or "information visualization" refers to an approach to exploratory data analysis that employs a variety of techniques which utilize human perception; techniques which may include graphical presentation of large amounts of data and facilities for interactively manipulating and exploring the data.

The present invention provides tools and methods for manipulating very large data structures, generally in the form of tabular or spreadsheet type data structures, to organize relevant data for ready visualization by a user attempting to visually identify correlations, trends or other insights among the data. Although the techniques described below use manipulation of heat map visualizations as an example of how the invention can be used, the invention is not limited to heat maps or gene expression data, as any numerical data can be accommodated with the methods and tools described herein.

In addition to providing the data to be analyzed in a readily viewable format, the present invention may also integrate additional data such as annotations, other kinds of experimental data, clinical data, and the like. Using the present techniques, most if not all relevant data can be inspected simultaneously in graphical form. The data can be easily and quickly manipulated by sorting or re-ordering rows and/or columns of the data to expose meaningful correlations and trends in the data which can be easily observed as a result of rearrangement.

FIG. 1 shows an example of a portion of a conventional heat map visualization 200 that is currently available to users. A standard heat map visualization such as visualization 200 is a static visual representation of a tabular data structure of gene expression values, wherein color-codings are used for displaying numerical values. The numerical value for each cell 202 in the data table is encoded into a color for the cell, although the colors are not apparent in the figs, of this application in order to comply with figure drafting rules generally requiring black and white figs. Instead, colors of the cells are represented by reference numerals, e.g., 202r represents a red colored cell and 202g represents a green colored cell. Color encodings run on a continuum from one color through another, e.g. green 202g to red 202r or yellow to blue for gene expression values.

Standard heat map visualizations have significant shortcomings as to their usefulness for performing visual correlation analyses. Since these displays are static, the cells in the display 200 cannot be manipulated to form different combinations or views in attempting to find similarities among the experimental data. Although a commonly owned product, known as Synapsia (available from Agilent, Palo Alto, Calif.) provides some limited capability such as simple column sorting or column rearrangement of a heat map, there remains a need for greater manipulation of the data such as provided by the present invention. Further, as noted above, the sheer volumes of data that are generated by current experimental data generating procedures, such as microarray procedures and protein expression measurements, for example, make it generally impossible to display the contents of all the data that needs to be reviewed on a single display. This further complicates any hope for visually identifying similarities among experiments or gene expression values, since not only is side-by-side visualization of potentially similar data values not currently possible through use of an automated technique, but the user must additionally switch between screen views to search for similarities, which eliminates the potential for simultaneous viewing of many of the possible combinations of the data.

FIG. 2 shows a screen display 100 resultant from using a visualization system according to the present invention, in which the same microarray experimental data used in the example described with regard to application Ser. No. 10/209,477 were used, except that the data associated with all thirty-one DNA gene expression microarrays was loaded into the system of the present invention. Only a portion of the display is shown, in order to meet the minimum print size limitations of the drawing rules. The experimental display portion 110 of the visualization 100 is designed to appear as a typical heat map visualization, so that users will be comfortable with viewing and interpreting the data. Unlike a typical heat map visualization, however, the experimental display portion is not a substantially static display, but may be manipulated to gain insight into correlations and similarities among the data displayed, as will be discussed in more detail below. Unlike the display in application Ser. No. 10/209,477, the experimental data in display portion 110 is not compressed, and therefore not all of the experimental data is shown, since there will be 8,066 cells of experimental values for each of the arrays 1, 2 . . . 31 displayed in the experimental display portion 110. However, using the manipulation techniques described below, the system is designed to reorder the data to group relevant data so that most if not all relevant data can be viewed on a single display 100.

In addition to the experimental data, clinical data and patient data are included in portions 120 and 130 of the visualization 100 adjacent matrix 110 shown in FIG. 2. The column 43 labeled "Unigene" contains the Unigene Cluster ID that further identifies the CDNA having been deposited on the microarray, with respect to each of the respective cells in each array 1-31. Thus, for example, Unigene Cluster ID "Hs 23590" is associated with the first row of experimental data 110 as shown in FIG. 2. This identifier is linked to that particular row of array data, so that if the row is reordered within the array, the Unigene Cluster ID is also reordered to the same row that the data assumes, to maintain accuracy of the characterizing clinical data. Likewise, the column of clinical data containing the cloneID (i.e., "Clone") 44 for the CDNA having been deposited on the microarray with respect to each individual microarray reading is linked to the particular row of experimental data that it describes and moves with that row when the row is repositioned. All other columns of clinical data share this characteristic. Columns 46, 48, 50 and 52 contain Name, BNS Symbol, BNS Description, BNS Chr data for each gene having these identification data in its row. The BNS columns 48, 50 and 52 contain information that is all imported from a commonly owned biological naming system, which is described in more detail in co-pending and commonly owned application Ser. No. 10/154,529 filed May 22, 2002 and titled "Biotechnology Information Naming System", which is hereby incorporated in its entirety, by reference thereto. The BNS columns 48, 50 and 52 are only examples of additional descriptive or annotative data that may be displayed along with the experimental data according to the present invention, and the present invention is in no way to be limited to inclusion and use of BNS information in each instance of use of the present invention.

The BNS_Symbol column 48 contains symbols which identify the particular gene in that row that the expression data is being presented for. Examples of such symbols appearing are SLC16A4, HOXd3, ATR, etc. The BNS_Description column 50 contains identifiers which are similar to those in the Name column 46, namely the short descriptive names of the genes. In most cases the BNS_Description column 50 and Name column 46 will contain the same information in respective rows, but since the BNS data is more official and recent, there might be slight differences or updates. The BNS_Chr column 52 identifies the cytogenic chromosome location of the gene in the row in which the information appears. All BNS data is derived from NCBI's LocusLink.

It should be noted that the present invention is not limited to capturing and visualization of the particular types of clinical data identified above, as they are only examples. Any textual or numeric data that can be associated with the experimental data can be added into the visualization.

The visualization 100 normalizes the data displayed which helps to make a more compact set of data to be displayed. Thus, for example, unlike the de-normalized display described above with regard to application Ser. No. 10/209,477, the Unigene Cluster ID "Hs 23590" does not have to be displayed individually for each array included in the display (i.e., thirty-one times, one for each cell in the first row of the experimental data shown), but rather is displayed only once for the row of that experimental data.

Additionally, data such as patient data or clinical data can be included in rows adjacent the experimental data display portion 110. In the example shown in FIG. 2, the first four columns of the display 100 incorporate clinical data and data measured from tissue samples. Row R1 includes invasive ability values for particular arrays of data, which correspond to the de-normalized invasive ability values in the visualization created by application Ser. No. 10/209,477 (note: this visualization is shown in FIGS. 2 and 3 of application Ser. No. 10,403,762), and row R2 indicates vasculogenic mimicry, where a "+" symbol in a cell of row R2 indicates that the data in the microarray in the column with which that cell is aligned exhibits vasculogenic mimicry and a "−" symbol in a cell indicates that the data in the microarray in the column with which that cell is aligned does not exhibit vasculogenic mimicry. An indication in a cell with the symbols "±" indicates that there was a mixed measurement. These symbols and their meanings are also referred to and explained in Bittner et al., "Molecular classification of cutaneous malignant melanoma by gene expression profiling", Nature, vol. 406, August, 2000, which is incorporated herein, in its entirety, by reference thereto. Row R3 includes cell motility values for those arrays that had this measurement taken. Row R4 displays the sex of each patient represented by each microarray, where "M" symbolizes male, "F" symbolizes female, and "U" symbolizes that the sex of the patient was not recorded.

Like the additional data in the columns of the display 100 (e.g., columns, 43, 44, 46, 48, 50 and 52) the additional data in the rows which characterize the experimental data (rows R1-R4 in the example of FIG. 2) is also normalized. For example, the indicator "M" displayed in the "Sex" row R4 is indicated only once, but pertains to each of the 8,066 cells in the microarray column 1 with which it is aligned.

Likewise, each value in each row of data (clinical data, patient data, etc.) associated with the experimental data display 110 is normalized, in that it is only indicated once, in one cell of the row, and pertains to each experimental data cell underlying that cell (e.g., to all of the data in that microarray column, in the case of the example shown in FIG. 2). Note also that the cells which overlap or intersect the additional rows and columns of non-experimental data (in the upper left hand corner of FIG. 2) are left blank, as they are neither adjacent a row of experimental data nor a column of experimental data. The first column of these cells has been conveniently used to identify the rows of the non-experimental data (rows R1-R4). It should be noted that the present invention is not limited to capturing and visualization of the particular types of clinical data and tissue sample data identified above, as they are only examples. Any textual or numeric data that can be associated with the experimental data can be added into the visualization.

The experimental data 110 can be sorted by column or by row, using the cross-hairs 112, 114. When performing a sort, in this example, only the experimental data is considered to determine the sort order, while the non-experimental data follows the repositioning of the rows or columns of data as they are resorted. For example, if a user selects the column highlighted by cross-hair 112 for performing a sort by column, only the rows containing the experimental data (i.e., heat map style visualization display 110 in FIG. 2) are sorted, and the clinical data in rows R1-R4 is locked, since the columns of experimental data that they pertain to do not change their positions in the matrix. Likewise, the clinical data in the columns adjacent the experimental data are not considered for sorting, but are reordered to follow the reordering of the rows of experimental data that results from the sort.

Figure 3:
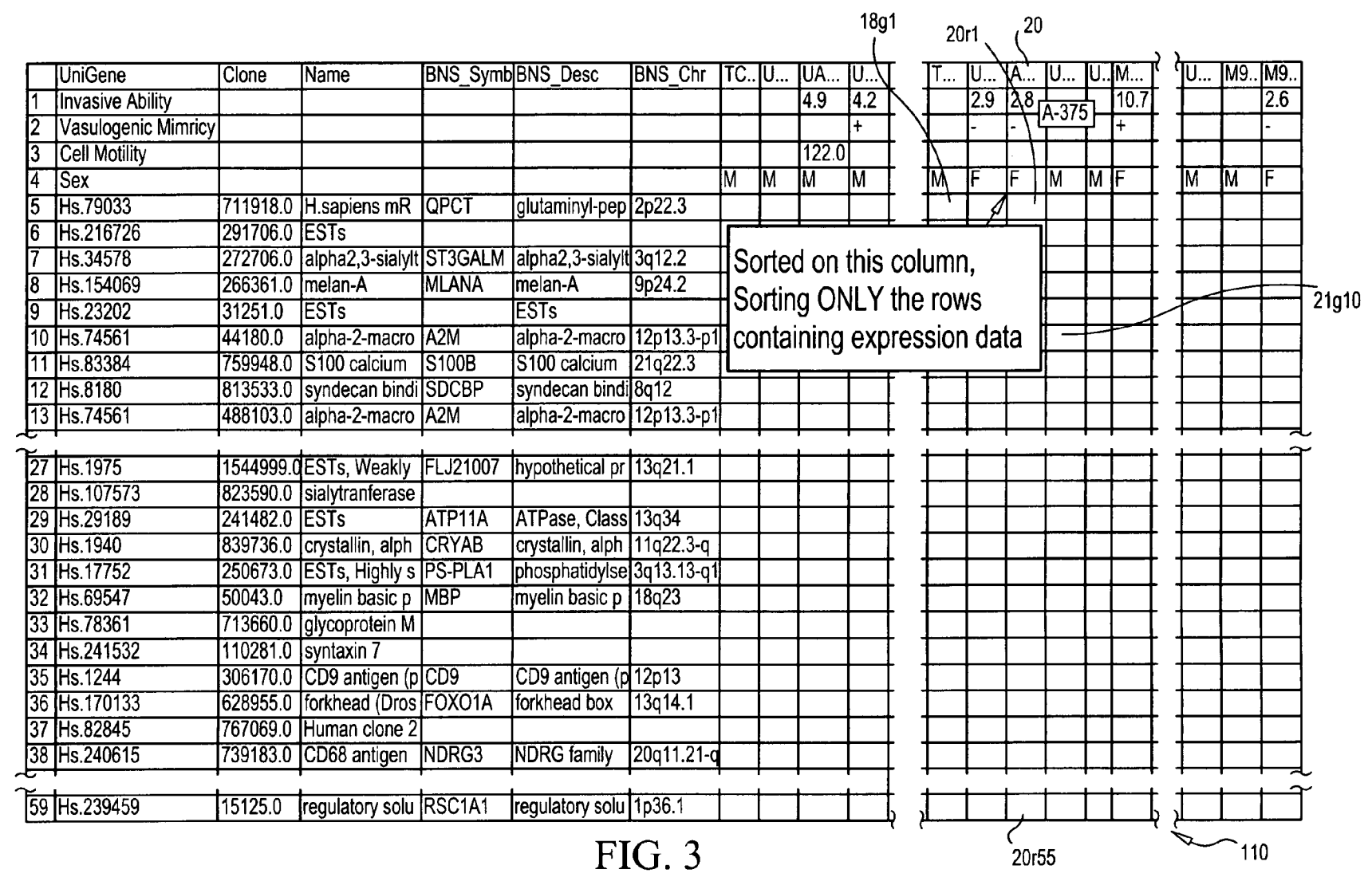

For example, FIG. 3 shows the results of a column sort that was conducted with regard to column 20 of the experimental data. In this example, the cells in column 20 have been sorted according to the cell with the highest degree of up-regulation (which is color-coded red according to the normal heat map visualization schema), with subsequent cells in descending order of expression value down to the lowest value. Of course, the present invention is not to be limited to sorting from highest up-regulated cell, as a reverse sorting order could be performed. Again, because each column has 8,066 cells, not all of the cells are shown in the visualization of FIG. 3, nor are all the columns shown due to constraints imposed by drawing rules. Because the sorting has been performed on the basis of the expression values in column 20, all fifty-three of the cells that are displayed for column 20 are red (20r1 through 20r55). As each of the cells in column 20 are rearranged according to the sort order determined, the entire row of experimental data assumes the same row placement as that of the reordered cell of column 20. Also, the non-experimental data and identification data in the left side of the visualization remains linked with the respective rows that it originally pertained to, and is rearranged according to the sort order of the cells in column 20. In this way, the identifying information/non-experimental data in the cells of columns 42, 44, 46, 48, 50 and 52 remains in the same row relative to the experimental data after re-ordering, thereby maintaining the accuracy of the normalization scheme.

FIG. 3 readily reveals a large concentration of up-regulated expression values, particularly in the upper right portion of the display 110, with some microarray columns having more dissimilar data values than others (see for example, green cells 18g1 and 21g10). However, a general observation that can be made from this sort is that the patients/microarrays on the right side of the matrix 110 appear to have more similarities to microarray/patient column 20 than those on the left side of the matrix 110.

Figure 4:
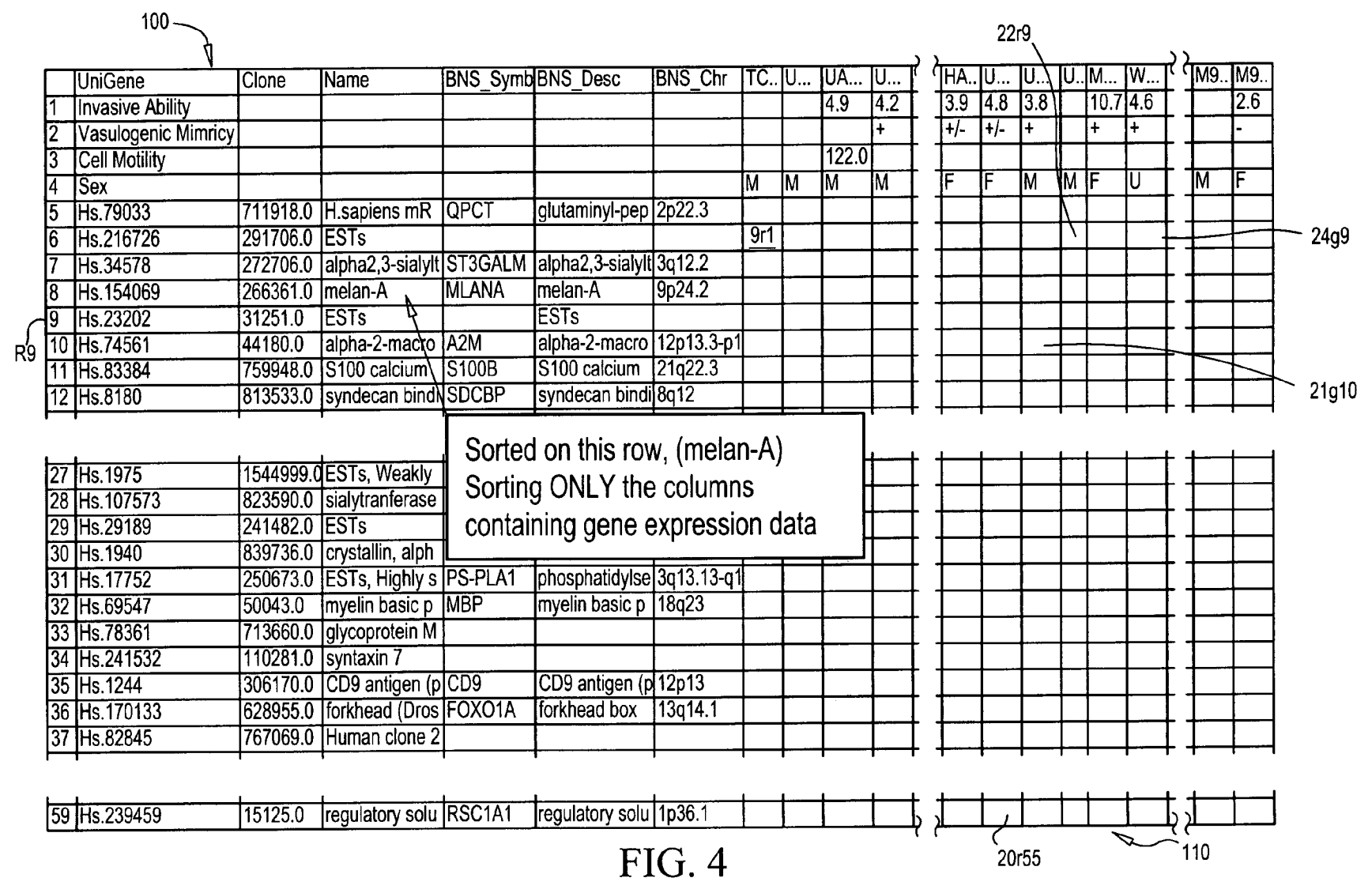

FIG. 4 shows the display order resulting after a row sort that was performed after the column sort described above with regard to FIG. 3. In this example, the sort was performed by outlining the row corresponding to the melan-A gene (row R9) with the cross-hair 114 and selecting a row sort operation. In effect, this row sort operation sorts the cells of row R9 (but only those cells residing within the experimental data portion 110 of the matrix 100), with the left-most cell belonging to the microarray having the highest up-regulation expression value, which, in this case belongs to the microarray that was originally displayed in experimental data column 19 in FIGS. 2-3. Accordingly, the array originally placed in experimental data column 19 was reordered or repositioned to assume the position of experimental data column 1 in FIG. 4 and the cell corresponding to the melan-A-gene therefore assumed the first cell position 9r1 in the sorted row. Of course, all of the other corresponding cells in the microarray originally positioned in column 19 are moved to the same respective rows in column 1 so that the entire microarray is represented in column 1. Like the column sort described above, this row sort was performed according to an order displaying the highest up-regulated cell (9r1) first (i.e., the left most cell of the row), with the second cell having the next highest expression level and so forth, down to the lowest expression value in column 31 of row R9. Once again, it is noted that the present invention is not to be limited to sorting from the highest up-regulated cell, as the sort could be based on the lowest expression level, and arranged in an ascending expression level order, for example. When sorting by row according to the data set shown in FIG. 4, the entire results of the sort order of the melan-A-gene can be viewed in row R9, since only 31 microarrays are included in the experimental data (although not all columns are shown in FIG. 4, for reasons already mentioned). Of course, not all rows are displayed, as indicated above, since this would require some compression scheme, or an extremely large display to represent all 8,066 rows of experimental data.

As noted above, the row sort was performed on the basis of the expression values in row R9 (i.e., Melan-A gene). As each of the cells in row R9 are rearranged according to the sort order determined, the entire column of experimental data assumes the same column placement as that of the reordered cell of row R9. Also, the non-experimental data and identification data in the top portion of the visualization remains linked with the respective columns that it originally pertained to, and is rearranged according to the sort order of the cells in row R9. In this way, the identifying information/non-experimental data in the cells of rows R1-R4 remains in the same row relative to the experimental data after reordering, thereby maintaining the accuracy of the normalization scheme. The non-experimental data on the left side of the visualization 100 remains locked, as it is normalized with respect to the rows of experimental data, which were not reordered in this manipulation.

The results displayed in FIG. 4 show that the user has in effect sorted a group of up-regulated genes (color-coded red in this case) into the upper left corner of the display 110. This sort by melan-A did a fair, but slightly imperfect sorting of the two classes of melanoma patients, as it can be seen that the group on the left side of the display 110 contains a lot of highly up-regulated values, while the group on the right side contains more neutral (e.g., colored coded black or a dark shade of red or green, such as cell 22r9 which is dark red and cell 24g9 which is dark green. Other rows surrounding row R9 in some of the microarrays on the right side also show a large disparity from the concentration of up-regulated cells in the upper left portion of the display 110, owing in part to the previous column sort. For example, column 22 contains a large number of down-regulated or green color-coded cells.

Melan-A is known to play a role in melanoma (hence the name), but if this had been a newly discovered gene, the display in FIG. 4 could have provided an insight to the user as to the potential discovery of a gene which plays an important role in melanoma. Similar to the previous case, the supplementary data in columns 1-7 are essentially locked in place and only the expression data are sorted.

The present invention supports both row and column sorting, as described above, as well as limited column and row reordering. This limited column and row reordering may be accomplished manually by the user. To accomplish manual reordering, the user can drag-and-drop rows and columns. This is accomplished by simply clicking the column or row header and while holding down the mouse button, dragging it left or right (column) or up or down (row) to its new location.

FIGS. 5A-5B contain a flow chart which outlines basic procedures for preparing and displaying a visualization 100 using the system according to the present invention, and for the manipulations of the data displayed, such as described above. In step S1, experimental data is inputted into an "n×m" matrix to be displayed as the display portion 110 shown in FIGS. 2-4, for example, where "n" is a positive integer representing the number of columns in the matrix, and "m' is a positive integer representing the number of rows in the matrix. Experimental data may be loaded from external sources including, but not limited to, DNA microarray experimental results, relative protein abundance measures derived from mass spectrometry and protein fragment data derived from gel electrophoresis experiments. Experimental data may be loaded as a tab-delimited text file, although the present invention is not limited to this format for loading the data. All data that is seen in the display may be loaded from such a single flat file (tab-delimited text file). Additional lines in the file specify the source experimental data type (e.g., for gene expression values this would be ratio or log-ratio), as well as the position in the full table where the first experimental data representation is to appear (i.e. the row and column). For example, the flat file and system may assume that all experimental data is in the lower right of the table and all annotations appear above or to the left of the experimental data.

In addition to the experimental data to be graphically represented on the display, all other data associated with the experimental data is also loaded and correlated into the system. For example, p-values, error analysis statistics, and other associated values may be loaded. Any ratio-based data or other data represented by numerically orderable measurements may be graphically represented and manipulated according to techniques described in the present specification.

Non-experimental data such as that displayed in rows R1-R4 can be loaded in a normalized scheme, in step S3 in an "n×y" matrix, where "n" is a positive integer representing the number of columns in the matrix, which will be displayed as an extension of the columns displaying the experimental values of the n×m matrix, and "y" is a positive integer representing the number of rows in the matrix. The "n value" (i.e., n=1, 2, 3 . . . n) of each column of the n×y matrix is linked to the corresponding "n value" in the n×m matrix in step S5, so that when a column of the experimental data is reordered by a sort, the column in the n×y matrix which corresponds to the column of experimental data that is reordered is reordered along with it to maintain the proper identification of each column of experimental data by the correct non-experimental data. This linking may be accomplished via BNS-like mechanisms that can match up identifier schemes (even when they are different, as long as a mapping between them exists). In some simple cases the identifiers may be consistent between the two data sets and it is only required that the identifier column is known. This may be by convention (e.g., the first column of every table must be a gene identifier derived from Unigene). Another way of accomplishing the linking is to require the user to identify the column to be used for linking, at the time that the data is imported for use by the present system in creating a display and manipulating the data displayed therein. Still another technique for linking is to program the software to analyze the data as it is imported and determine if a column contains recognizable identifiers. For example, the system may scan all the data during import and determine that all entries in a particular column have a recognizable identifier (e.g., all entries in column two start with "Hs.") and so are probably Unigene identifiers and can be used to accomplish the linking. Another example is that all entries may start with "NM_" and so are refseq mRNA identifiers, which can be used as a basis for the linking. Although the last technique described is highly domain specific, it provides useful functionality for users in that domain.

It should be further noted that steps S3 and S5 are optional, i.e., the present invention can display experimental data and reorder the data as described herein without the necessity of including non-experimental data in rows corresponding to the experimental data. The rows of non-experimental data however, when available, add further information to be viewed by the user in a single display.

Similarly, in step S7, non-experimental data such as that displayed in columns 42, 44, 46, 48, 50 and 52 in FIGS. 2-4, for example, can be loaded in a normalized scheme, in a "z×m" matrix, where "z" is a positive integer representing the number of columns in the matrix, and "m" is the number of rows of the matrix, which will be displayed as an extension of the rows displaying the experimental values of the n×m matrix. The "m value" (i.e., m=1, 2, 3 . . . m) of each row of the z×m matrix is linked to the corresponding "m value" in the n×m matrix in step S9, by techniques similar to those described above with regard to column linking, but with common row identifiers, so that when a row of the experimental data is reordered by a sort, the row in the z×m matrix which corresponds to the row of experimental data that is reordered is reordered along with it to maintain the proper identification of each row of experimental data by the correct non-experimental data. It should be further noted that steps S7 and S9 are optional, i.e., the present invention can display experimental data and reorder the data as described herein without the necessity of including non-experimental data in columns corresponding to the experimental data. The columns of non-experimental data however, when available, add further information to be viewed by the user in a single display.

After constructing the underlying matrix as described above, which serves as the basis for displaying the visualization 100, the data from the matrix is displayed in a single visualization made up of a k×j matrix (step S13, FIG. 5B). The k×j matrix will generally be limited by the capacity of the monitor or display upon which the visualization is outputted, and may be predetermined by the display software. It is generally preferable to display as much data as can be reasonably viewed by the user without over-taxing the eyesight, and it is generally preferable, although not absolutely necessary, to display all of the non-experimental data and all of the columns of the experimental data, so that, for example, in FIGS. 2-4, at least a portion of the data from each microarray is visible. According to this preference, "k" would be a positive integer equal to the sum of "n" and "z", i.e., k=n+z. Note that some or all of the non-experimental data may need to be abbreviated or cut off, but a tooltips feature may be provided so that when a user hovers the mouse sprite over a compressed, abbreviated or cut-off representation of non-experimental data in a cell, a pop-up display of the full expression of the non-experimental data is displayed. Also, if "n+z" is a value greater than a preset maximum value for "k", then some of the columns of the experimental data may not be displayed, although these values will still be considered in performing manipulations and they may be displayed upon reordering of the columns of experimental data. As to the number of rows displayed in the visualization, the display will be generally inadequate to display all of the rows in examples where the experimental data represented is microarray data or protein abundance data for example. In these instances "j" is an integer equal to the number of rows that can be reasonably visualized on the display and can be preset in the software, but will be less than the sum of "m+y". Generally, the system is arranged so that all of the rows of non-experimental data are displayed, while only a first portion of the "m" rows of experimental data is displayed. The experimental data and non-experimental data in rows higher than "j" are accessible by the manipulations of the data, but will only be displayed upon reordering, when one or more rows of the experimental data has been determined by a sort to be of particular interest. The situation where not all columns of experimental data can be displayed does not occur as frequently as the situation when not all the rows may be displayed. For example, when considering microarray data, each column pertains to a microarray and the number of microarrays to be considered can be easily controlled by the user.

Upon viewing the display 100, if the user decides to perform a column sort at step S15, then the user outlines a row of the experimental data display 110 in step S17 (i.e., the $a^{th}$ row of the total "m" number of rows, where "a" can be any integer from "1" to "j" of the experimental data) which contains data of interest upon which the user desires to perform the column sort. The outlining may be accomplished by aligning the cross hair 114 as described above, or by other visual indicating means. Upon selecting the $a^{th}$ row, as described, each experimental data value (i.e., cells one through n of the $a^{th}$ row, noted as cells 1, a through n, a in step S19) are compared to perform a new sorting order, whether the cells are to be arranged in descending order of value or ascending order of value. This sorting schema is an iterative process in which the first cell is compared with the second to determine the sorting arrangement and then either the first or second cell, whichever is determined to be of lower value according to the sorting schema is compared with the value of the third cell, and so forth, and can readily be accomplished by one of ordinary skill in the art. It is important to note, however, that cells one through z of the $a^{th}$ row of the z×m matrix are not considered or compared during the sorting procedure, as they contain non-experimental data that would be meaningless or erroneous to compare with the experimental data values during the sort.

After completing the sorting procedure, the cells in the $a^{th}$ row are assigned their new column order designation, and all cells in each column of the n×m matrix are assigned the same new column number as the cell in the $a^{th}$ row that they share a column with. Also, in step S21, the columns of non-experimental data in the n×y matrix are reassigned new column numbers that correspond to the new column numbers of the experimental data columns that they are linked with. In step S23, the columns of the n×m matrix and the n×y matrix are rearranged or reordered synchronously to be visually displayed in the display 100 according to the new ordering scheme.

If the user decides to perform a row sort at step S25, then the user outlines a column of the experimental data display 110 in step S27 (i.e., the $b^{th}$ column of the total "k" number of columns displayed, where "b" can be any integer from "1" to "k") which contains data of interest upon which the user desires to perform the column sort. The outlining may be accomplished by aligning the cross hair 112 as described above, or by other visual indicating means. Upon selecting the $b^{th}$ column, as described, each experimental data value (i.e., cells one through m of the $b^{th}$ column, noted as cells b, 1 through b, m in step S29) are compared to perform a new sorting order, whether the cells are to be arranged in descending order of value or ascending order of value. This sorting schema is an iterative process like the one described above with respect to the column sort. It is important to note, however, that cells one through y of the $b^{th}$ column of the n×y matrix are not considered or compared during the sorting procedure, as they contain non-experimental data that would be meaningless or erroneous to compare with the experimental data values during the sort.

After completing the sorting procedure, the cells in the $b^{th}$ column are assigned their new row order designation, and all cells in each row of the n×m matrix are assigned the same new row number as the cell in the $b^{th}$ column that they share a row with. Also, in step S31, the rows of non-experimental data in the z×m matrix are reassigned new row numbers that correspond to the new row numbers of the experimental data rows that they are linked with. In step S33, the rows of the n×m matrix and the z×m matrix are rearranged or reordered synchronously to be visually displayed in the display 100 according to the new ordering scheme.

The user can choose to manually reposition (step S35) one or more columns or rows by dragging-and-dropping row(s) and/or colunm(s) at step S37, in the manner described above.

Similarity Sorting

The column, row and manual sorting procedures described above can be useful in identifying correlations, trends and other relationships among the data in some instances. However, when dealing with large volumes of experimental data, such as microarray data sets or protein or other molecular data sets, the data sets are often sufficiently "noisy" that it is often difficult to find meaningful correlations by simply sorting a single column (e.g., a single array) or a single row (e.g., a single gene). When experimental data such as these are measured by very low level signals, there may be a lot variation in the measured values from experiment to experiment and they are inherently "noisy". Microarrays are generally noisy due to a number of experimental variances. Microarrays are generally qualitatively reproducible, but the individual measurements will still show quite a bit of variance. Thus, if a sort is performed on the basis of a single or individual array, slightly different ordering results are observed, as compared to the same sort performed on an array which is already known to be similar. These differences may even occur when a sorting procedure is performed on two different arrays representing the same experiment (i.e., a replicated experiment) due to differences in noise levels between the two arrays. To address these problems, the present invention further provides the capability of performing similarity sorting, which includes the ability to sort the data set by row or column similarity.

Similarity sorting of a row differs from the standard row sorts described above, in that a similarity calculation is performed between a selected row of experimental data and each non-selected row of experimental data to compare each entire non-selected row to the entire selected row to determine how close or similar it is to the selected row, and then the rows are ordered in terms of their similarity ranking with respect to the selected row, which assumes the position of row 1. As to similarity column sorting, an entire selected column of experimental data is compared with each entire non-selected column of experimental data to determine similarity rankings and the selected row assumes column 1 with the remaining columns following in position according to their similarity ranking. The rows and columns of non-experimental data are treated in the same manner that they are treated for standard row and column sorts, so as to maintain association with the appropriate rows and columns of experimental data.

FIG. 6A shows a simple 3×4 matrix which will be used to refer to a very simple demonstration of similarity sorting according to the present invention. The 3×4 matrix represents an experimental data set, i.e., an "m×n" matrix as described above with regard to FIGS. 5A-5B. Of course, the actual experimental data sets which will generally be treated by the present system and methods will be much larger, such as the 31×8,066 matrix referred to in the examples above, but a 3×4 matrix has been shown to greatly simplify an explanation of the procedures, while at the same time, explaining the concepts and techniques required, which can then be readily applied to larger data sets.

A similarity column sort or similarity row sort may be performed on any of the columns (101, 102, 103) or rows (201, 202, 203, 204) that the user so selects. Thus, for example, assume a user wishes to perform a similarity sort on row 202. By selecting row 202 in FIG. 6A, such as by using the cross hair 114 or other indication means, such as by right clicking on a column or row header or cell representing an experimental data value, the system invokes a popup menu 180, as shown in FIG. 6B. Popup menu 180 gives the user options, among others, of performing a standard sort or a similarity sort. In the view shown in FIG. 6B, a similarity sort has been selected, and the system at this time provides further options as to whether the similarity sort is to be performed according to the current row selected 185 or current column selected 186. Although not shown, selection of a standard sort would provide the same options (i.e., as to row or column based sorting), and sub-sorting as well as next neighbor sorting options may also be provided in the popup menu 180 or a similar popup feature. After selecting a similarity row sort in this example, the system rearranges the matrix of experimental data such that row 202 becomes the first row positioned in the matrix as shown in FIG. 6C. Any non-experimental data (e.g., data in the z×m matrix characterizing rows 201 and 202 which happen to be the only two rows that were repositioned at this stage) is repositioned so as to maintain the positions relative to the experimental data prior to the row reordering.

The experimental values expressed in the cells of the rows are then compared by a similarity test, to determine the relative similarity of each of rows 201, 203 and 204 to row 202. One method of determining relative similarity is to calculate the squared Euclidean distance of each row 201, 202, 203 from row 202 and then sort the rows 201, 202, 203 according to the squared Euclidean distance, with the row having the smallest squared Euclidean distance being positioned adjacent row 202 and the row having the next smallest squared Euclidean distance from row 202 being positioned adjacent that column, with the largest distance in this example being ordered as the last row.

In the example chosen in FIG. 6C, the squared Euclidean distance between rows 202 and 201 would be calculated as follows:

$$D(202,201)=[(101,202)-(101,201))^2+((102,202)-(102,201))^2+((103,202)-(103,201))^2$$

Where:
D is the squared Euclidean distance value;
D(202,201) represents the squared Euclidean distance value between rows 202 and 201;
(101,202) represents an experimental data value in cell 101,202 of row 202 that is being used for purposes of determining similarity;
(101,201) represents an experimental data value in cell 101,201 that is being used for purposes of determining similarity; and so forth.

After determining D(202,201), D(202,203) and D(202,204) are calculated using the same approach. The values of D(202,201), D(202,203) and D(202,204) are then compared to rank order them with respect to row 201. The lowest value determines the next row to be positioned immediately beneath row 201, with the second lowest value being placed beneath that, and so forth. Thus, in the above example, assuming that the calculated value for D(202,203) is less than the calculated value for D(202,201) which is less than the calculated value for D(202,204), i.e., D(202,203)<D(202,201)<D(202,204), then the reordered matrix according to the similarity row sort described would appear with row 202 in the top row, followed by rows 203, 201 and 204, in that order, as shown in FIG. 6D. Similar to the standard row sorting, any cells containing non-experimental data adjacent the rows 201-204 are not considered for the Euclidean distance calculation (or any other similarity algorithm that may be employed). However, the adjacent, non-experimental data that is linked with these rows is reordered respectively with the reordering of the experimental data in those rows to maintain the normalized schema.

Alternatively to Euclidean distance, other measures of similarity may be performed in conducting similarity sorting as described above. For example, an alternative distance based on the Pearson correlation coefficient may be computed as follows:

$$r = \frac{\sum X_i Y_i - \frac{\sum X_i \sum Y_i}{N}}{\sqrt{\left(\sum X_i^2 - \frac{(\sum X_i)^2}{N}\right)\left(\sum Y_i^2 - \frac{(\sum Y_i)^2}{N}\right)}}$$

where
X=a first column or row being considered for similarity measurement,
Y=a second column or row being considered for similarity measurement,
N=the total number of X or Y values in a column or row X or Y, and
the distance is measured as 1−r.

The Euclidean measurement technique described may be desirable for finding rows (or columns) which are closely similar in overall amplitude, while the Pearson correlation coefficient may be more desirable for sorting and separating correlated and anti-correlated rows (or columns), though similarity in this approach is weighted more toward the overall pattern or shape of an expression profile, rather than its amplitude. In any case, the user may select among similarity measurements and may choose to approach the data with more than one type of similarity measurement, to compare and contrast the results achieved.

A similarity column sort may be conducted in a very similar manner to that described above with regard to a similarity row sort. The column selected by the user may be repositioned in the first or leftmost column and then similarity calculations may be conducted between experimental data in the selected column and each remaining column of experimental data to determine a reordering of the columns by their similarity to the selected column. Similar to the standard column sorting, any cells containing non-experimental data adjacent to the columns 101-103 would not be considered for the Euclidean distance calculation (or any other similarity algorithm that may be employed). However, the adjacent, non-experimental data that is linked with these columns would be reordered respectively with the reordering of the experimental data in those columns to maintain the normalized schema.

Figure 7:
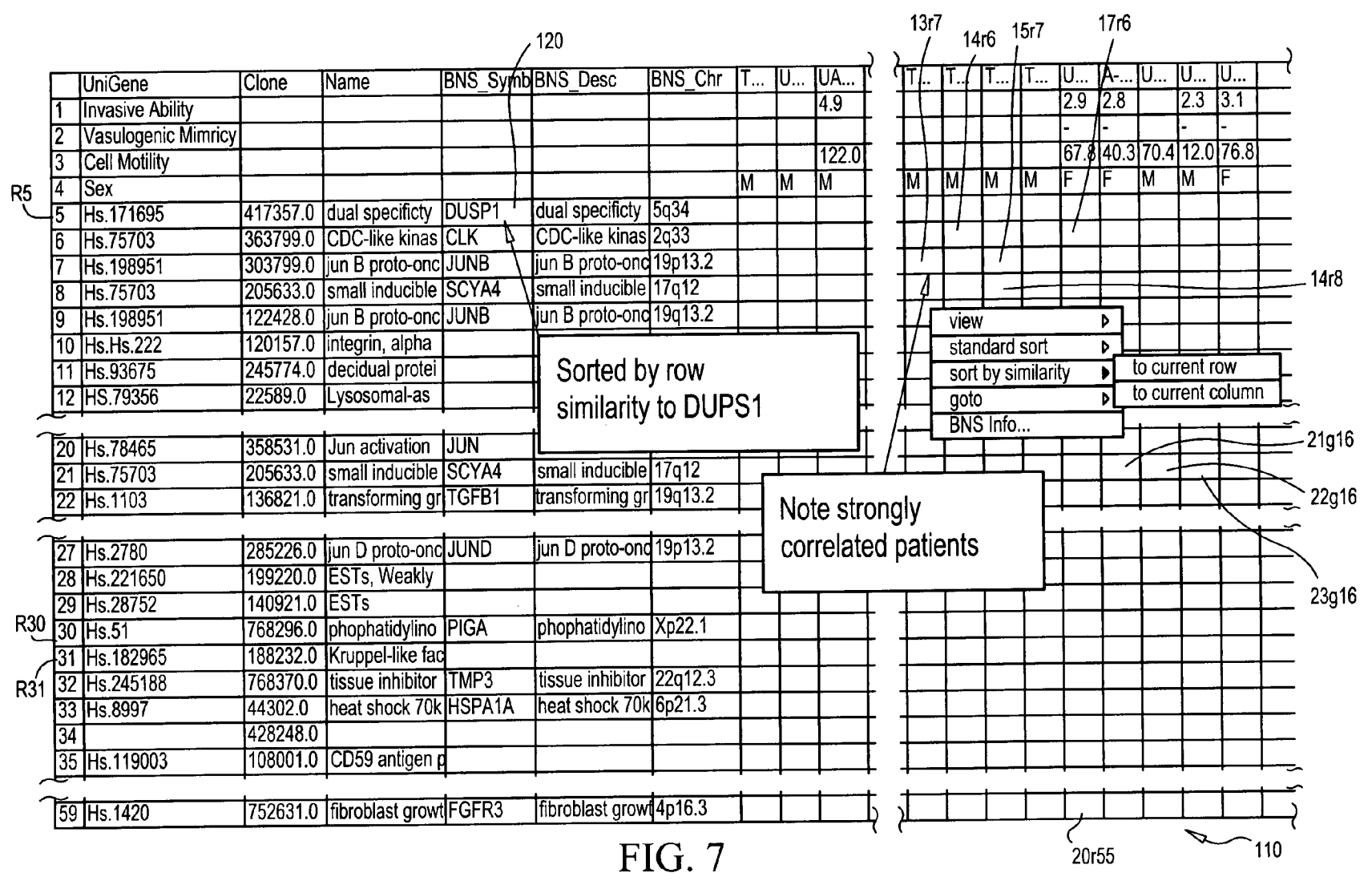

It should be noted that since the similarity reordering is done based upon similarity to the selected row or column, not all adjacent rows are necessarily most similar to one another. This is especially true as the number or rows or columns increases. Thus, for example, in FIG. 7, the results of a similarity row sort based upon the gene "DUSP1" (selected row appears in row R5) is shown. In this case, for example, rows R30 and R31 aren't necessarily very similar to each other, as they are ranked based on their similarity to row R5. Rather, what the order indicates is that the gene expression values in row R30 are more similar to those in row R5 than the similarity between row R31 and row R5, i.e., D(R5,R30)<D(R5, R31). However, the overall result of such a sort reorders the genes based on their aggregate similar behavior across many microarrays in the case of microarray experimental data.

When calculating the squared Euclidean distances, there are several considerations that apply to the present procedures that do not necessarily apply generally to the calculation of a Euclidean distance between two points of data in any Euclidean space. With regard to microarray experimental data, all distances are computed in log space to avoid biasing toward up-regulated genes. With two dye microarrays, data are generally stated as ratios of some sample treatment relative to some standard. If the data are expressed as a simple ratio, then values are always positive with up-regulated ratios being greater than one and down-regulated ratios having a value less than one but greater than zero. A simple example will confirm that the use of such ratios would tend to overweight up-regulated genes when determining D. For example, assume in FIG. 6C that the expression values of each of cells (101,202) and (102,202) is one, i.e., normal or neutral, that the expression value of cell (101,201) is 2× down-regulated, i.e., has an expression ratio value of 0.5, and that the expression value of cell (102, 201) is 2× up-regulated, i.e., has an expression ratio value of 2. If we consider the squared distance contribution between cells (101,202) and (101,201) as well as the squared distance contribution between cells (102,202) and (102,201) as would be done in the course of determining an overall squared distance value between rows 202 and 201, we obtain the following:

$$((\mathbf{101,202})-(\mathbf{101,201}))^2=(1-0.5)^2=0.25$$

$$((\mathbf{102,202})-(102, 201))^2=(1-2)^2=1$$

Thus, it can be seen that the overall contribution to the sum of the squared distances which determines the similarity between the entire rows, is much more heavily weighted by the up-regulated gene expression ratio, even though the down-regulated ratio is separated from a "normal reading" by the same factor (2×) as the up-regulated expression ratio. To eliminate this biasing factor, log ratio expression data is used in the similarity calculations, or if expression ratio data is displayed, then the expression ratio data is first converted to log expression ratio data. By using log expression ratio data, both up and down regulated genes are symmetric with respect to absolute magnitude and no bias towards up-regulated genes occurs in the similarity calculations.

Another consideration is that a true Euclidean distance is measured by the square root of the sum of the accumulated squares of the measurement differences taken. However, since the goal of the procedures according to the present invention is only to determine a relative sorting value of rows or columns based upon relative distance to a selected row or column, and not to determine actual distances from the selected row or column, the sum of the squared differences between corresponding cells is sufficient, and the square root of the sum need not be determined. Since the same relative results can be determined without calculating the square root values, the square root calculation may be dispensed with.

In calculating differences between corresponding cells, differences involving cells that have invalid or missing data are treated as if the difference is 0 so that it does not unduly contribute one way or the other to the overall value of D used in determining similarity. In effect, this treatment defaults to assuming similarity of the missing data, rather than imposing some exaggerated notion of arbitrary dissimilarity in these instances. Although this treatment may give somewhat less than precise results, the situations where data is invalid or missing in a cell must be addressed in some fashion, and as long as the amount of missing data is small in comparison to the rest of the distances calculated, the effect is negligible. Alternative ways of addressing these situations include allowing the user to select what action to take in such cases and either use the current approach or eliminate the data, or treat the distance as some fixed value other than zero.

In the unlikely event that the D values for two rows or columns turn out to be equal, the ordering of these two rows with respect to one another is arbitrary (having been determined to both have equal similarity to the selected row/column) and therefore the system arbitrarily places the lower numbered row or column nearer to the selected row or column, with the second row or column having the equal similarity value following.

It is further noted that the similarity sorting procedures described above are only one approach to reordering data based on similarity among entire rows or columns of data. Various other approaches to manipulating the experimental data based upon characteristics of entire rows or columns may be readily applied by the instant invention. As just one further example, a similarity sorting order can be computed to group "nearest neighbors" of rows or columns. According to this approach, the selected row or column is positioned first followed by the row or column with the shortest squared Euclidean distance or other lowest valued sorting criteria (i.e., nearest neighbor). The third row or column is selected based on its determination as the nearest neighbor to the second row or column and positioned adjacent thereto, and so forth. According to this procedure, all rows or columns are calculated for similarity or proximity to the selected (first positioned) row or column, just as in the above-described procedure, to determine positioning of the second row or column. However, this approach varies for placement of the third and subsequent rows/columns. For the second and subsequent row/column positions, the distance/proximity calculations are repeated or iterated wherein the row/column positioned just filled is treated as the selected row/column. For example, for placement of the third row/column, the second placed row or column is used to determine distances/proximities with respect to all remaining rows/columns except the first row/column which has already been placed. By this iterative treatment of the data, what results is an ordering wherein the second row/column is the nearest neighbor of the first row/column; the third row/column is the nearest neighbor of the second row/column; the fourth row/column is the nearest neighbor of the third row/column, and so forth, as contrasted with the previously described procedures where each row/column is ordered based upon its relative similarity to the first column/row. By this approach, each adjacent row/column is positioned so as to be relatively similar to its neighbors and this provides an additional view by which the user might identify emerging trends among the experimental data.

It should be further noted that similarity sorting using the squared Euclidean distance between the selected column or row and the remaining columns or rows is only one algorithm that can be employed in determining similarity sorts (according to a selected column/row, by nearest neighbor, or otherwise) by the entire row or column. Many other algorithms, measures and schemes may be used to accomplish a reordering of the experimental data based upon entire rows/columns cumulatively. For example, weighting factor(s) based on experimental error statistics could be used so that very noisy measurements don't contribute to the overall measure as much as more reliable data. Similarity measures that utilize more than one data type for performing similarity computations may also be employed (e.g. combine microarray-generated ratio data with TAQMAN measurements, etc.). Other techniques readily suggest themselves, and standard data-mining techniques and algorithms can be applied to sort rows and columns by various criteria. However, the key property of such sorting should be that it's fast enough to be reasonably interactive to allow for user directed data browsing. If the computation is too time-consuming then it should be performed by more traditional non-interactive modes of data mining. A significant advantage of the current algorithms implemented is that they are very fast to compute and thus are virtually as interactive as a typical column sort.

Another variation for performing similarity sorting is to allow user selection of the distance measure. For instance, the user might chose as an option to calculate squared Euclidean distance with or without error weighting. Another option provides an embedded scripting environment that allows the user to design a custom measure scheme, which would then become one of the optional methods. Other similarity algorithms may alternatively be employed to determine a similarity ranking for display of the experimental data according to the present invention.

Further, although the examples above describe performing the similarity sorts based upon the displayed experimental data values (such as the gene expression values displayed by color-coding in the example of microarray data), similarity sorting can also be accomplished based upon other values associated with the experimental data values that are primarily displayed in the matrix. These types of sorts can be accomplished as a primary sort to display similarity of the experimental data based on the associated values, or can be accomplished secondarily to a similarity sort performed first by using the displayed experimental data values. For example, in the case of microarray data, a similarity sort may be performed based upon the displayed gene expression ratios, after which a further similarity sort (based on the same selected row or column) may then be performed based on error statistics, p-values, standard deviations, or other secondary data types associated with the expression ratios, wherein the values of the secondary data type selected are used to determine squared Euclidean distance values or other similarity sorting values.

Sub-Sorting

To further extend the flexibility and versatility of the present invention for providing various arrangements of experimental data likely to expose trends, correlations or other relationships among the experimental data when viewed by a user, the experimental data may be sub-sorted either after performing any of the sort procedures described above or even initially after displaying the experimental data as loaded. The sub-sorting procedures may be the same as described above with regard to any of the sorting procedures. Sub-sorting procedures differ from those described earlier in that the row or column selected by the user for sub-sorting is not re-positioned to the first row or column space of the matrix 110. Rather, the selected row or column maintains its current position upon selection, and only rows/colunms subsequent to this position are considered for the sub-sort (i.e., rows below the selected row or columns to the right of the selected column). The previous rows or columns are left in the same positions as prior to the sub-sort procedure and are therefore unaltered by the sub-sort.

The user interaction for performing a sub-sorting procedure is effectively the same as described above with regard to various methods of similarity sorting, except that upon selecting a row or column, the user chooses the sub-sort function, and specifies a row-based or column based sub-sort, whereby the selected row/column maintains its present location and the subsequent rows/columns are reordered based upon similarity calculations carried out. By iteratively using this sub-sorting method in conjunction with standard sorting procedures, the user can create ad-hoc groupings of similar matrix elements. This has the effect of something similar to user-directed clustering, but is much less mathematically rigorous and therefore much faster for real time interactive use. The groupings have meaning only to the user constructing them and care must be taken not to over-interpret what they signify. Still, they may provide insight into the relationships within the underlying data, or at a minimum provide some method for mathematically grouping related items.

Similarity Sorting Based on Non-Experimental Data

The procedures and techniques described above with regard to similarity sorting of the experimental data may also be applied to non-experimental data, to provide similarity sorts based on the non-experimental data that provide insights to similarities between various rows or collections of the experimental data. In many cases the non-experimental data, which accompanies and describes the experimental data that is displayed, may be represented by a binary set of values, for example, "yes/no", "true/false", "male/female", "±", etc. For example, a row may be provided to characterize whether the samples from which the experimental data are taken are diseased or not (which may be represented by "yes/no" or "±", for example) or whether the samples have been drug treated or not (the values of this row may also be represented as "yes" or "no"; or "+" or "−", for example), or whether the sample is taken from a female or male (values of this row may be represented by "F" or "M", for example). These are only examples of non-experimental data meeting the binary criteria and are in no way limiting of the present invention, as there are many more categories of information that may be used. The classification of such non-experimental data may be clinical, phenotypical, computational (e.g., partitions derived computationally, see Bittner, M et al., "Molecular Classification of Cutaneous Malignant Melanomas by Gene Expression Profiling", which was incorporated by reference above), or other descriptive data characterizing the data in matrix 110. Further, classification data may even be experimental data that is not a member of the set of experimental data included in matrix 110 (e.g., experimental data describing the experimental data in matrix 110).

Figure 8:
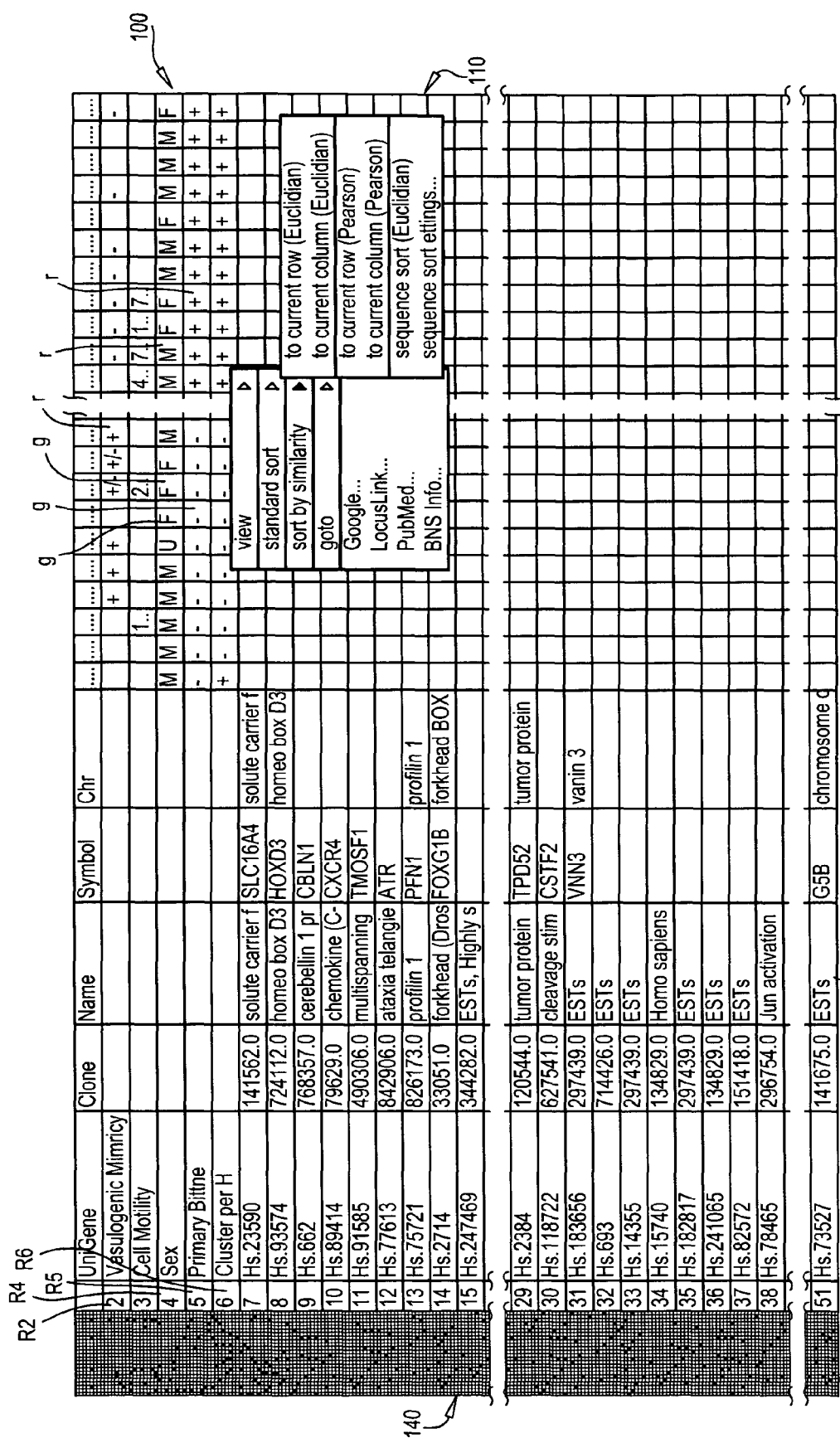
FIG. 8 shows a display generated from the same data used to generate the views in FIGS. 2-4 and 7, and shows color-coded binary data for use in constructing pseudo-data vectors according to the present invention.

In the example shown in FIG. 8, the same data is displayed as in the examples described above with regard to FIGS. 2-4 and 7. In this example, the non-experimental data rows titled "Vasculogenic Mimicry" (row R2), "Sex" (row R4), "Primary Bittne . . . " (row R5) and "Cluster per H . . . " are all represented by binary classifications. Upon recognition of the binary patterns, the present system may highlight the binary values with color coding, to represent a row of pseudo-experimental data. For example, in FIG. 8, the cells containing the value "+", as well as the cells containing the value "M"

have been highlighted in a light shade or red or pink ("r") so as to visually distinguish these values from actual experimental data cells having upregulated values, but to simulate upregulated cell values. Similarly, cells containing the value "−", as well as cells containing the value "F" have been highlighted in a light shade of green ("g") so as to visually distinguish these values from actual experimental data cells having downregulated values, but to simulate downregulated cell values. Cells which contain neither of the binary values (e.g., see the cell with an unspecified value "U" in row R4) may be either left unshaded, or may be shaded light black or grey to represent a neutral value. Note that the viewer 100 in FIG. 8 also includes a generalized view of all of the experimental data in a compressed experimental data matrix 140, in the manner described with regard to FIG. 15 of parent application Ser. No. 10/403,762, while at the same time providing a non-compressed view of a selected portion of the experimental data in matrix 110.

In order to perform similarity sorting against a selected row of data that is classified according to a binary classification scheme (such as any of rows R2, R4, R5 and R6 noted above), a user selects a row of binary classified classification data as a row of interest to serve as a basis for the sort procedure. The system then produces an imaginary row of expression data, also referred to as a row of pseudo-experimental data, based on user settings for values to be applied to the existing binary values. FIG. 9A shows an example of a menu item provided the user for setting the pseudo-values of the binary data according to the user's preferences. In the example shown, the user has selected row R6 ("Cluster per H . . . ) as the row upon which to perform the similarity sort. Menu 300 provides a selection 302 for setting the positive value of the binary values, as well as a selection 304 for setting the negative value. In this example, the user has assigned an 8.0 fold increase value to the positive value (i.e., "+", in this example), and an 8.0 fold decrease (i.e., 1/8.0) value to the negative binary value (i.e., "−", in this example). The positive and negative values are settable by the user so that if the user wants to create a pseudo-experimental vector with relatively extreme amplitudes, the negative and positive values can be set relatively high. On the other hand, the user may choose lower values to create a vector with lesser amplitude swings. Any values that are non-reported (i.e., neither "+" nor "−", in this example) may be automatically assigned a null value, which is a value of one, for purposes of gene expression ratio measurements, since they are generally normalized log ratios. Thus, an expression ratio of one corresponds to no up or down regulation. For datasets that are not characterized by ratio values or log ratio values, however, the system may substitute a null value of zero.

Figure 10:
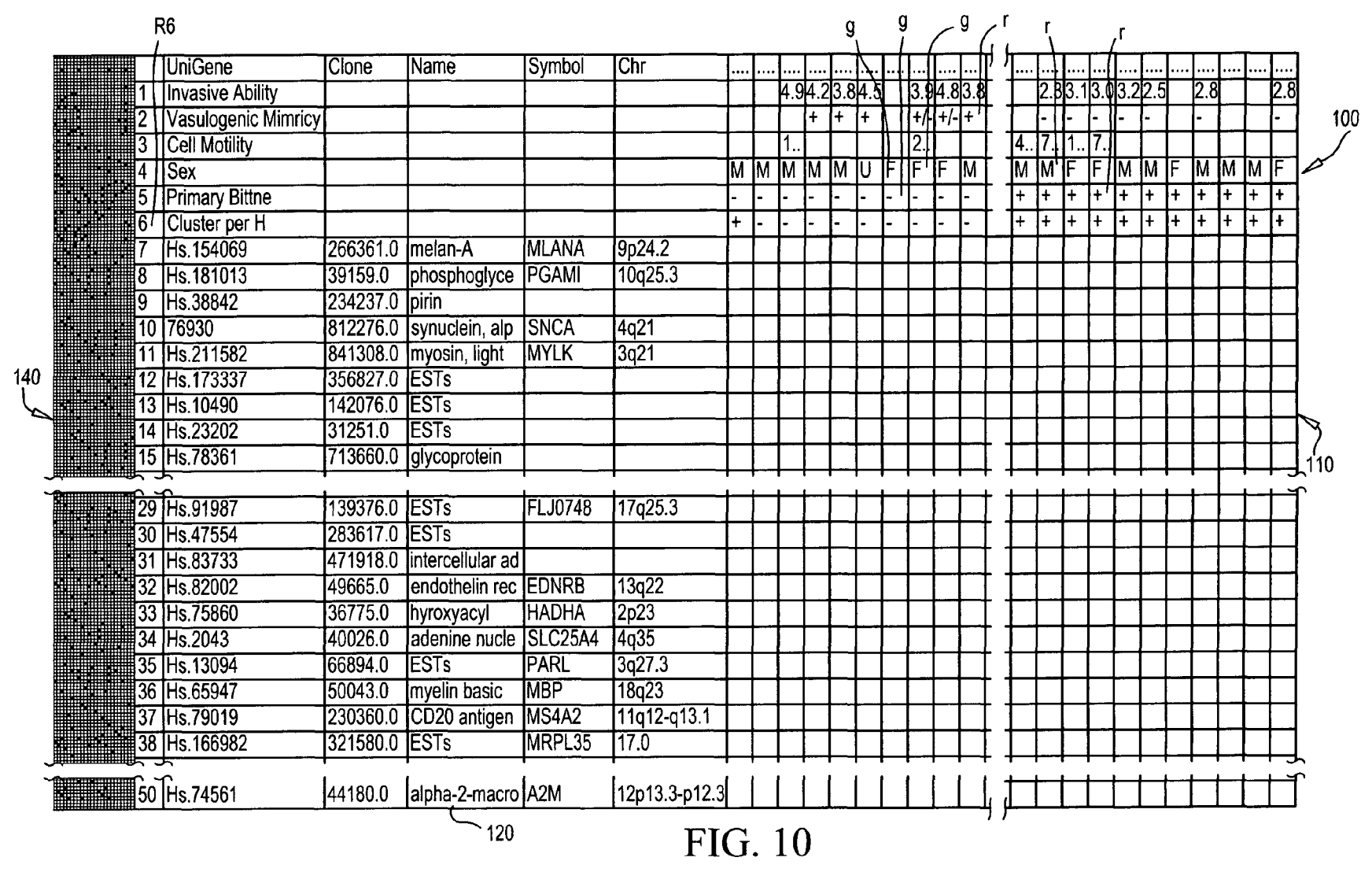

By substituting the assigned values for the binary symbols, a pseudo-experimental or expression vector is constructed, against which the expression levels of the other experimental data rows can be compared and similarity or distance calculations may be performed. As shown schematically in FIG. 9B, a classification row 320 having binary values is converted to a pseudo-experimental vector 330 by substituting the values assigned by the user in the sort settings menu 300. A similarity sort is then conducted in the same manner as described above with regard to sorting with respect to a row of experimental data, by calculating distances between experimental vectors 324, 326 and 328 each with pseudo-experimental vector 322 and then reordering the rows based upon the calculated distances. FIG. 10 shows the results of a similarity sort carried out against row R6 with the positive and negative values set as described. Thus a similarity sort was performed against a binary classification of two classes of melanoma based on clustering the gene expression data for each. It can be seen that the "melan-A" gene was determined to be the closest in similarity to the pseudo-expression vector constructed from row R6, as noted by its position at the top of the list, just under row R6 (i.e. in row 7) in FIG. 10. Other similar genes follow "melan-A" and are in qualitative agreement with the results shown in FIG. 4.

Thus, sorts against binary classifications of non-experimental data may be used by the present system to do similarity sorts. This capability may be particularly useful when the user has not already become aware of any knowledge with respect to any particular gene that might be indicative of a characteristic being searched, such that there is no specific gene to begin a similarity search with, absent the user randomly picking a gene to begin with. Rather, in this case, the user can perform a similarity search on a characteristic that may be known to be important, where such characteristic is represented by binary non-experimental data. More broadly, this capability provides a more general starting point for beginning a similarity search, for whatever reason the user may wish to proceed in this way. By running the similarity sort discussed with respect to FIG. 10, this procedure was validated, since particular genes which were known in this example to be relevant to the classification sort were ordered in positions close to row R6, thereby verifying the usefulness of this technique, since it did identify genes that were important to the characteristic searched upon.

It is further noted that meaningful similarity sorts have been successfully performed even upon incomplete information in a row of non-experimental data. For example, a similarity sort performed after converting row R2 of FIG. 8 produced results qualitatively similar to those produced computationally by Bittner et al. (see Bittner, M. et al., "Molecular Classification of Cutaneous Malignant Melanoma by Gene Expression Profiling", referred to and incorporated by reference above), in that the same highly discriminating genes were identified from the overall dataset, as being significant to the sort that was carried out. Thus, even though the binary information for "Vasculogenic mimicry" (row R2) is only known for some cell lines, the conversion to a pseudo-experimental vector substituted values corresponding to ratios of one for the unknown values, as noted. The resulting vector still contained sufficient information to identify relevant genes. It is further noted that the current software may be set to toggle between assignments of the user set positive and negative values, so that the order inverts each time a sort is run. For example, when set in toggle mode, a first similarity sort may produce a pseudo-experimental data vector by assignment of the positive set value to "+" values in a class of binary data and by assignment of the negative set value to the "−" values in the binary data. Then, on the next successive search, the system assigns the positive set value to the "−" binary values and assigns the negative set value to the "+" binary values in the binary data. This enables sorting both possible constructions of the pseudo-expression vector with the same simple user interface.

Similarity Sorting Based on Ad-Hoc Non-Experimental Data

Similar sorting procedures may be carried out in an ad-hoc manner wherein the user supplies an arbitrary or completely user generated row of pseudo-expression/pseudo-experimental data. For such a procedure, an empty row of supplemental data may be provided or created in display 100, into the cells of which the user may then enter the user's own binary classification or other expression values. The manually entered row of pseudo-experimental data may then be used for similarity sorting in the manner described above.

By allowing the entry of arbitrary expression values (as opposed to binary classifications) this further extends the capabilities of similarity sorting based on a row of pseudo-experimental data. For example, non-binary classifications may be represented, in situations where the user may construct a computation or intuitive means for determining what expression values correspond to what classifications. For example, a user may construct vectors for three classes (e.g., no disease, mild disease, aggressive disease, etc.). Since vectors of this sort are generally very likely dependent on context, it is more difficult to do automatically as was done in the binary classification examples above, and is preferably done by manual input.

Ad-Hoc Similarity Sorting Based on Pseudo-Experimental Data Vectors Derived from Experimental Data The system allows a user to identify a select group of cells (e.g., a group of cells from a row of experimental data, from which a pseudo-experimental data vector is then generated for use as a basis for similarity sorting. This type of search may be useful in an instance, for example, where the user knows that certain particular columns in the matrix 100 identify samples known to be important to a process being studied, for example, a group of columns may be tissues taken from a tumor registry and the experiments may be studying a particular type of cancer. In this case, the cells aligned with the columns identifying tumor registry samples are likely to be affected or upregulated upon occurrences of the particular cancer being researched. Therefore, by searching those rows that distinguish the selected columns from the remaining columns of the experimental data, this is likely to find a cluster of related expression data vectors. It should be noted here that the cells selected for creation of a pseudo-experimental data vector are typically contiguous cells in a row of experimental data, although they need not be. The same techniques can be carried out on non-contiguous cells in a row of experimental data, contiguous cells in a column of experimental data, or non-contiguous cells in a column of experimental data.

Figure 11A:
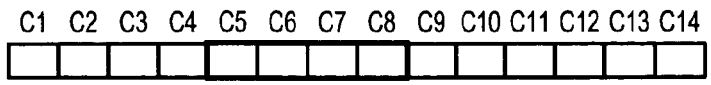
FIG. 11A is a schematic representation of an example of a row of experimental data from which cells are selected to calculate a pseudo-data vector.
Figure 11B:
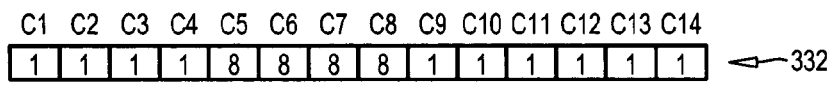
FIG. 11B shows the resultant pseudo-data vector, after conversion of the selection shown in FIG. 11A.
Figure 11C:
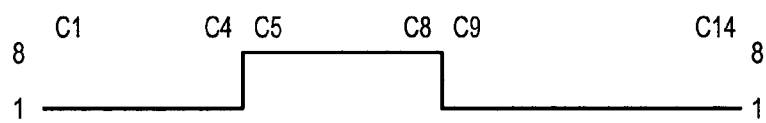
FIG. 11C is a graphical representation of the positive and neutral values applied in constructing the pseudo-data vector of FIG. 11B.

Referring now to FIG. 11A, a schematic representation of an example of a row of experimental data from which cells are selected is shown. In this example, assume that the user has determined or has made an assumption that the cells in columns five through eight (i.e., C5-C8) may bear some significance in relationship to the phenomenon being studied. As such, the user selects cells C5-C8 in the row of experimental data to generate a pseudo-experimental data vector therefrom. The system next generates the pseudo-experimental data vector by setting the values of cells C5-C8 to each have the positive ratio value (e.g., 8.0, or whatever the user set the value at in the sort settings) assigned in the sort settings (see FIG. 9A). The remainder of the cells are set to a value corresponding to a ration of $\frac{1}{1}$ (or alternatively to the low setting value) as shown in FIG. 11B. The resultant pseudo-experimental data vector is then used as a basis for similarity sorting all rows of experimental data in matrix 110 against it and the resulting distances are ranked, after which the order of the experimental data rows are repositioned according to distance rank, with the closest row being represented in row 1, etc. Thus, the pseudo-experimental data vector 332 in this case, functions as a type of window or filter that emphasizes the data values in columns 5-8, while deemphasizing all other columns, as illustrated in FIG. 11C. The visualization of the reordered rows may be insightful to the user, who may note similarities between nearby rows and/or perform further sorts to further study the matter, based on the user's visualization. Further sorts may be based on any of the techniques described herein, and are not limited to further sorts of the same type.

Multi-Step Similarity Sorting Based on Pseudo-Experimental Data Vectors

The creation and use of pseudo-experimental data vectors may be further applied to systematically probe for specific patterns of data within a dataset. By constructing more than one pseudo-experimental data vector to perform similarity sorts against, this technique is useful where a user may expect patterns to emerge across groups of data, such as may be expected for time series experiments, for example. Referring again to FIG. 9A, the user selects values for window size 306, increment 308 and similarity increment 310 that are used as a basis for constructing the pseudo-experimental data vectors and for carrying out this multi-step technique. In the example shown in FIG. 9A, the similarity sorts will step using a window size of "2", which, in this example indicates the number of columns to be considered during each step. However, it is noted that the same technique may be applied to searching a number of rows at a time, if it makes sense to search and perform similarity calculations in this fashion, based on the nature of the data that is represented in matrix 110.

The increment chosen for the example in FIG. 1 is "1", meaning that each new similarity sorting procedure will takes its considerations of data starting from the next column past the starting column of the previous similarity sorting procedure. Thus, in this example, the first sorting procedure considers columns one and two, the second sorting procedure considers columns two and three, the third sorting procedure considers columns three and four, and so fourth. The procedure may end when there is no more data to sort, e.g, when there are not a sufficient number of columns to fill the window size, or when there are no rows remaining to be sorted. Alternatively, the procedure may stop when there are not a sufficient number of columns to fill the window size 306, or when there are not a sufficient number of rows to fill the predefined similarity increment number 310. Further alternatively, a predefined number of steps may be established prior to running a multi-step process, wherein the process would end after having completed a number of steps equal to the predefined number of steps.

It is noted that any number may be chosen for the window size, as long as it is less than the total number of columns (or rows, as the case may be) in the dataset. It makes no sense to choose a number larger than the total number of columns (or rows, as applicable). However, the window size may be chosen to be equal to the number of columns (or rows, as applicable), but there would be no iterations of pseudo-experimental vectors produced and similarity sorting procedures performed. However, it may be desirable to choose such a window size in order to perform a subsort of the first specified number of rows (or columns) of data, which would be governed by the similarity increment number 310 that is set, as will be apparent as the description continues below. Similarly, any number may be chosen for the increment 308, as long as the number is small enough that, when considering the window size, at least two similarity sorting procedures are performed. When the window size 306 and increment size 308 combine to make the number of columns or rows too great to successfully perform at least two sorting procedures, then this technique cannot be performed.

The similarity increment 310 setting determines the number of rows (or columns, if the window size is across rows) of results that will be maintained for each similarity sorting procedure. Thus, for the example specified in FIG. 9A, the first similarity sorting procedure is carried out after creating a first pseudo-experimental data vector wherein the first two cells of the vector are assigned the positive ratio value 302 of 8.0 and the remaining cells are each assigned the negative ratio value 304 of 1/8.0. A similarity sorting procedure is then carried out with respect to all rows of experimental data in the manner that has been described above. Then, upon considering the distance results, the first one hundred rows of experimental data are displayed at the top of the matrix 110 in descending order, for example, with the row having the smallest distance occupying row one.

Next, the increment value 308 of one is applied and a new pseudo-experimental data vector is calculated by moving the window size of two over by the incremental amount of one, along the columns of data in the matrix 110. Thus, the new pseudo-experimental data vector is characterized by having the first cell with the negative value 304 of 1/8.0, the next two cells are assigned the positive value 302 of 8.0 and the remaining cells are each assigned the negative value 304 of 1/8.0. Another similarity sorting procedure is then carried out with respect to all of the remaining rows of experimental data, excluding the one hundred rows that have already been ordered and displayed in the first one hundred rows in the matrix 110. Then, upon considering the distance results, the first one hundred rows of experimental data having the smallest distances as determined by the current similarity search are displayed in rows one hundred one to two hundred, in descending order, for example, with the row having the smallest distance occupying row one hundred one.

This procedure is continued until one of the stopping criteria have been met, as set forth in paragraph [00140] above.

Figure 12:
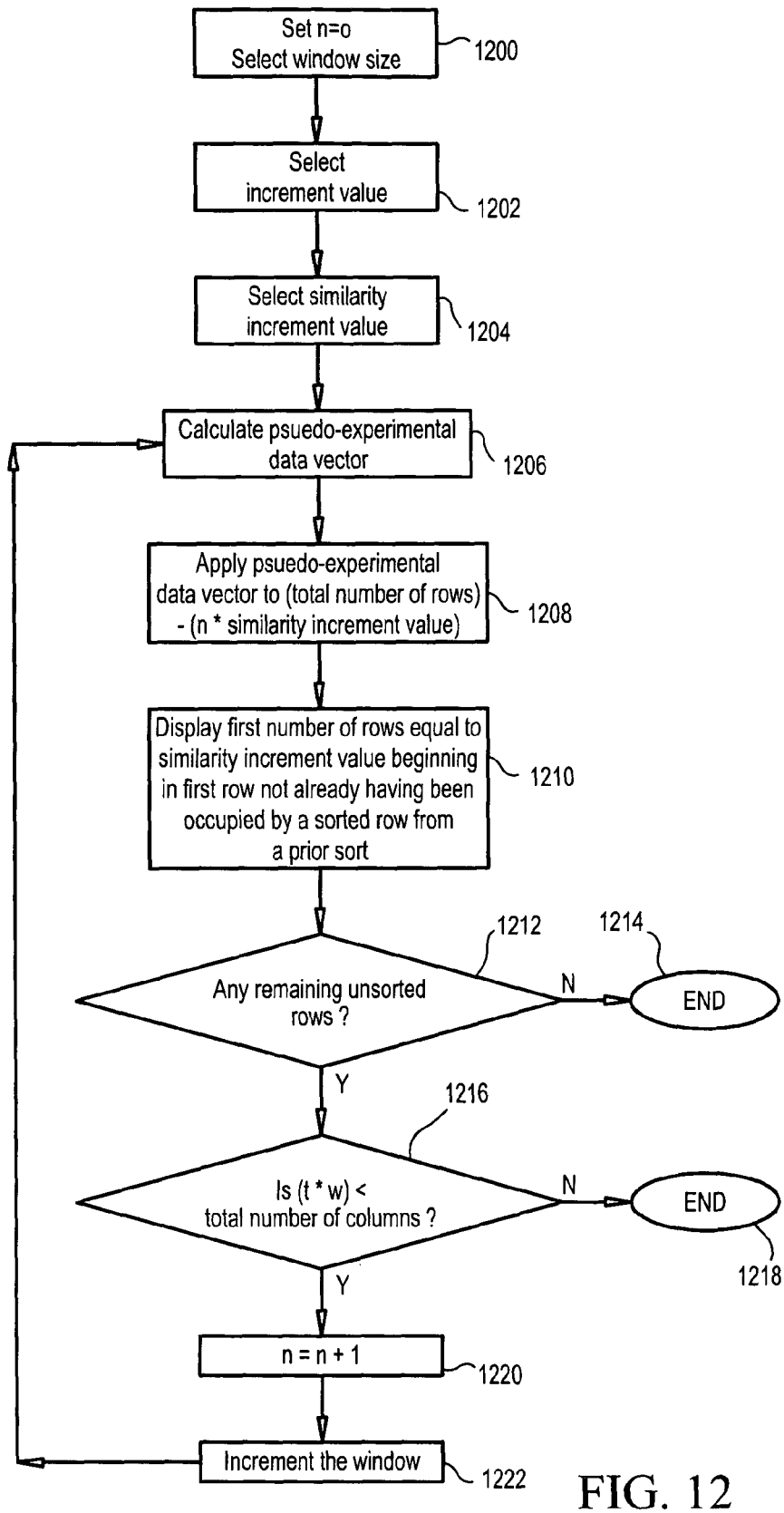
FIG. 12 is a flowchart exemplifying a multi-step similarity sorting process according to the present invention.

FIG. 12 is a flowchart exemplifying a multi-step similarity sorting process described above. Although this explanation refers to applying the window size to a number of columns, since that is the most recurring application of the procedure to expression data, it is again noted that the window could be applied to a number of rows to do similarity sorting procedures among columns of data. At event 1200, the user, in addition to having already preset the positive and negative values 302,204 to be applied in constructing a pseudo-experimental data vector, selects a window size that is used to emphasize a particular number of consecutive cells in each pseudo-experimental data vector. Also, at the beginning of the procedure, a counter for tracking the iterations performed by the system is set (e.g., n=0).

At event 1202, an increment value 308 is selected by the user which defines the number of columns that the window will increment with each iteration of the process. The increment value 308 may be chosen to provide overlapping placement of the window, as in the example shown in FIG. 9A. However, the increment may alternatively be chosen to place the window in adjoining positions (e.g., window size of two, increment of two), or to even skip column positions, as the situation may warrant (e.g., window size of two, increment of four).

At event 1204, a similarity increment value 310 is selected. The similarity increment value is generally a fraction of the total number of rows to be sorted, thereby allowing multiple sort procedures to be carried out. The size of the similarity increment value 310 will further generally be dependent upon the context of the data to be compared.

Next, a pseudo-experimental data vector is calculated at event 1206 in the manner described above. As noted, the cells currently identified by the window size are assigned the positive value 302, and all other cells are assigned the negative value 304.

At event 1208, a similarity sorting procedure is carried out, based on the pseudo-experimental data vector, with respect to the total number of rows, excluding any rows which have already been sorted and ordered. Thus, for the first iteration, n=0, and all of the rows are considered during the similarity sort. At event 1210, a number of rows equal to the similarity increment number are selected for ordering and display in the matrix, the rows having the smallest calculated distances being chosen and displayed in descending order.

Next, at event 1212, it is determined whether there are remaining rows of data, which have not been reordered (i.e., unsorted rows), upon which to carry out an additional similarity search. If there are no unsorted rows remaining, then the process ends at event 1214. If there are unsorted rows remaining (i.e., those that have not been already displayed as ordered sort results), then it is determined at event 1216 whether there are any columns remaining which have not been selected by the window as it is incremented, i.e., is the product of the number of increments times the increment size 308 less than the total number of columns? If the product of the increment number times the increment size is not less than the total number of columns, then the process ends at event 1218. If on the other hand, the product is less than the total number of columns, then the counter is incremented by one at event 1220.

At event 1222, the window is incremented by the preset increment value 308 and a new pseudo-experimental data vector is calculated at event 1206 to carry out another iteration of the similarity sorting process in the manner described above.

Figure 13:
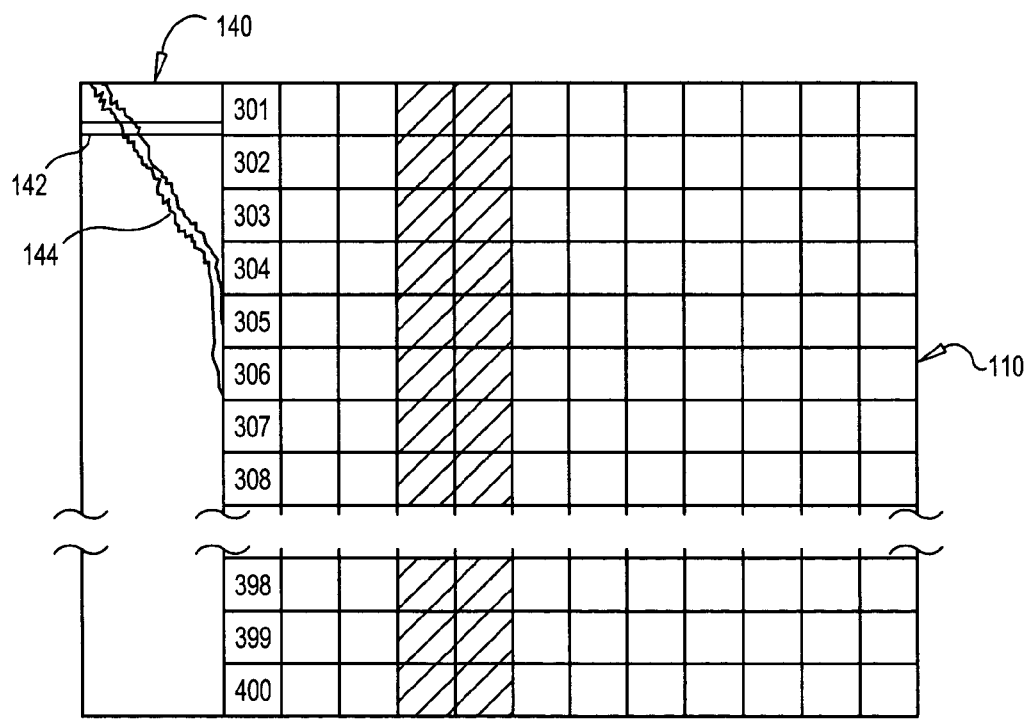
FIG. 13 is a schematic representation wherein a trend resulting from a multi-step sorting procedure is visualized in a compressed viewer that represents all of the data, while a non-compressed view displays the rows of data identified by a selection window in the compressed viewer.

As already noted this multi-step similarity sorting technique can be useful for identifying trends among time-sequenced data, or other data where similarities among incremental groups of the data are likely to occur. When a fairly large similarity incremental value is selected, it may be the case that the uncompressed view of the data in matrix 110 will not readily visibly display the trend, as it cannot visually display all of the rows on a single screen in such a case, as noted before. In such a case, the compressed view 140 may show a well-defined trend as it displays the macro view of all the rows. FIG. 13 is a schematic representation of this situation, wherein only the upregulated cells identified through the similarity sorting steps are represented in viewer 140 (due to drawing rule constraints). Viewer 110 displays the rows of data identified by the selection window 142, in an uncompressed manner. In the view shown, viewer 110 shows only the results of the third iteration of the process, wherein the cells in columns three and four are shaded to show the upregulated values that resulted in close distances to the pseudo-experimental data vector constructed from positioning the window over cells three and four. This data is highlighted by selection window 142 in the macro/compressed viewer 140. Further, the overall trend of the results of the multi-step sorts is identified by the upregulated cells 144, which are readily visible among the rest of the compressed data due to their color differentiation.

Alternative to the graphical representations of experimental data referred to, shown and described above, the present invention provides alternative methods and visualizations for the graphical representation of experimental data, including inkblot representations, or biasing graphical representations toward either finding correlations among rows or among columns, each of which are fully discussed in application Ser. No. 10,403,762. All of the tools, techniques and processes are fully integratable and functional with each and every one of such alternative types of graphical representation.

Further, the techniques and tools of the present invention may be employed to display data, including sort results in a highly compressed visualization, including highly compressed horizontal bar graph, highly compressed vertical bar graph, or any other highly compressed format also described in application Ser. No. 10,403,762.

Still further, the additional visualization features described in application Ser. No. 10,403,762 are also applicable to all of the features described herein. Such additional visualization features include linking with further sources of informational data to provide a more comprehensive characterization of the experimental data being examined, importing annotations; displaying or overlaying annotations or other pertinent information, mechanisms for combining related data of different types into a single unified visualization, linking of multiple independent viewers, and the like.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, data type, manipulation, manipulation order, process, process step or steps, to the objective, spirit and scope of the present invention. All such modifications are intended to be within the scope of the claims appended hereto.

That which is claimed is:

1. A computer-implemented method for displaying and manipulating data representing physical measurements, the method comprising:
   storing, in a storage element of a computer implementing said method, an ordered data matrix comprising:
      a plurality of measured values representing a plurality of different physical measurements performed on a plurality of samples;
      a plurality of sample descriptive values corresponding to each sample, each sample descriptive value characterizing a corresponding sample independent of said measurements; and
      a plurality of measurement descriptive values corresponding to each physical measurement, each measurement descriptive value characterizing a corresponding type of measurement or measurement condition, independent of said samples;
   providing a two dimensional detail graphic on a display of said computer, said graphic having a plurality of cells, each cell corresponding to one of said values in said data matrix, said graphic providing a view of a portion of said data matrix that is defined by a base location in said data matrix;
   generating a pseudo-data vector comprising one value for each of said samples, said pseudo-data vector being calculated from said plurality of sample descriptive values or from said plurality of measurement descriptive values, independent of said measured values representing said physical measurements;
   reordering said data matrix based on a measure of similarity between said pseudo-data vector and measured values of said data matrix; and
   displaying on said display a new portion of said data matrix based on said re-ordering.

2. The method of claim 1, wherein said pseudo-data vector is generated by assigning numerical data values to a selected portion of said sample descriptive values.

3. The method of claim 2, wherein said selected sample descriptive values comprise binary data.

4. The method of claim 2, further comprising color-coding cells of said selected sample descriptive values, said color-coding representing a function of the sample descriptive values in the cells.

5. The method of claim 2, further comprising color-coding cells of said selected sample descriptive values, said color-coding representing the binary values of binary data.

6. The method of claim 2, wherein at least one cell of said data matrix lacks a sample descriptive value, and wherein said generation of said pseudo-data vector further comprises assigning a predefined null value to said cell lacking a sample descriptive value.

7. The method of claim 3, wherein said binary data values in said selected portion of said sample descriptive values comprise annotative binary data values, and wherein said assigning numerical data values to a selected portion of said sample descriptive values comprises substituting predefined pseudo-data values for said positive and negative annotative binary data values.

8. The method of claim 2, further comprising inverting the numerical data values that are assigned to said selected portion of said sample descriptive values.

9. The method of claim 1, wherein said measure of similarity comprises calculating a distance value between the pseudo-data vector and a vector generated from a select set of said measured values.

10. The method of claim 9, wherein said distance value is determined by calculating a squared Euclidean distance between said two vectors.

11. The method of claim 1, wherein said calculating a pseudo-data vector comprises receiving values inputted by a user.

12. The method of claim 1, wherein said assigning numerical data values to a selected portion of said sample descriptive values comprises substituting a first predefined pseudo-data value for emphasizing each cell in a sub-portion of said selected portion of said sample descriptive values, and a second predefined pseudo-data value for de-emphasizing each remaining cell of said selected portion of said sample descriptive values.

13. The method of claim 12, wherein said first predefined pseudo-data value for emphasizing is a positive value inputted by a user.

14. The method of claim 12, wherein said predefined pseudo-data value for de-emphasizing is inputted by a user.

15. The method of claim 1, further comprising transmitting data representing a result obtained to a remote location.

16. The method of claim 1, further comprising receiving a result obtained from a remote location.

* * * * *

UNITED STATES PATENT AND TRADEMARK OFFICE
CERTIFICATE OF CORRECTION

PATENT NO. : 8,131,471 B2  Page 1 of 1
APPLICATION NO. : 10/688588
DATED : March 6, 2012
INVENTOR(S) : Robert Kincaid It is certified that error appears in the above-identified patent and that said Letters Patent is hereby corrected as shown below:

On the Title Page, Item (56), under "Other Publications", line 10, delete "Josepn" and insert -- Joseph --, therefor.

Signed and Sealed this
First Day of May, 2012

David J. Kappos
*Director of the United States Patent and Trademark Office*